United States Patent [19]
Gozes et al.

[11] Patent Number: 5,565,424
[45] Date of Patent: Oct. 15, 1996

[54] SUPERACTIVE VIP ANTAGONISTS

[75] Inventors: Illana Gozes, Ramat Hasharon, Israel; Douglas E. Brenneman, Damascus, Md.; Matityahu Fridkin, Rehovot, Israel; Terry W. Moody, Germantown, Md.

[73] Assignee: Ramot - University Authority for Applied Research and Industrial Development Ltd., Tel-Aviv, Israel

[21] Appl. No.: 194,591

[22] Filed: Feb. 7, 1994

[51] Int. Cl.$^6$ .............. A61K 38/16; C07K 14/00
[52] U.S. Cl. .............. 514/12; 530/324; 435/7.2; 435/7.21; 435/7.23
[58] Field of Search .............. 530/324; 514/12; 435/7.2, 7.23, 7.21

[56] References Cited

U.S. PATENT DOCUMENTS

| | | | |
|---|---|---|---|
| 4,605,641 | 8/1986 | Bolin et al. | 514/12 |
| 4,734,400 | 3/1988 | Bolin et al. | 514/12 |
| 5,196,315 | 3/1993 | Ronnett et al. | 435/29 |
| 5,273,963 | 12/1993 | Moody et al. | 514/12 |

FOREIGN PATENT DOCUMENTS

| | | | |
|---|---|---|---|
| 463450 | 1/1992 | European Pat. Off. | C07K 7/10 |
| 540969 | 5/1993 | European Pat. Off. | C07K 7/10 |

OTHER PUBLICATIONS

Gozes et al. Brain Res. vol. 540 p. 319 (1991).

*Primary Examiner*—Christine M. Nucker
*Assistant Examiner*—Benet Prickril
*Attorney, Agent, or Firm*—Townsend and Townsend and Crew LLP

[57] ABSTRACT

The present invention relates to a family of peptides encoding antagonists of the vasoactive intestinal peptide (VIP) designed to distinguish multiple receptors that mediate VIP neurotransmission, neurotrophism and cell division. The invention also relates to methods of using these peptides to antagonize VIP-associated activity and function. The invention further relates to pharmaceutical compositions dsigned to inhibit VIP-associated activity.

26 Claims, 6 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
    ( A ) LENGTH: 28 amino acids
    ( B ) TYPE: amino acid
    ( D ) TOPOLOGY: unknown ( i i ) MOLECULE TYPE: peptide ( i x ) FEATURE:
    ( A ) NAME/KEY: Modified-site
    ( B ) LOCATION: 17
    ( D ) OTHER INFORMATION: /note="Independently selected from
      the group consisting of naturally occurring amino
      acids and amino acid mimetics, provided that AA-19
      is not methionine."

( i x ) FEATURE:
    ( A ) NAME/KEY: Modified-site
    ( B ) LOCATION: 19
    ( D ) OTHER INFORMATION: /note="Independently selected from
      the group consisting of naturally occurring amino
      acids and amino acid mimetics, provided it is not
      methionine."

( x i ) SEQUENCE DESCRIPTION: SEQ ID NO:1:

```
Lys  Pro  Arg  Arg  Pro  Tyr  Thr  Asp  Asn  Tyr  Thr  Arg  Leu  Arg  Lys  Gln
1                  5                        10                           15

Xaa  Ala  Xaa  Lys  Lys  Tyr  Leu  Asn  Ser  Ile  Leu  Asn
                20                        25
```

( 2 ) INFORMATION FOR SEQ ID NO:2:

( i ) SEQUENCE CHARACTERISTICS:
    ( A ) LENGTH: 28 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:2:

```
Lys  Pro  Arg  Arg  Pro  Tyr  Thr  Asp  Asn  Tyr  Thr  Arg  Leu  Arg  Lys  Gln
1                  5                        10                           15

Met  Ala  Val  Lys  Lys  Tyr  Leu  Asn  Ser  Ile  Leu  Asn
                20                        25
```

SUPERACTIVE VIP ANTAGONISTS

FIELD OF THE INVENTION

The present invention relates generally to a family of polypeptides. More particularly, the present invention relates to a family of polypeptides which are antagonists of the vasoactive intestinal polypeptide (VIP). In addition, the present invention relates to the use of these polypeptides to inhibit VIP-associated activity.

BACKGROUND OF THE INVENTION

Vasoactive intestinal polypeptide (VIP) is a widely distributed peptide hormone which mediates a variety of physiological responses including gastrointestinal secretion, relaxation of gastrointestinal, vascular and respiratory smooth muscle, lipolysis in adipocytes, pituitary hormone secretion, and excitation and hyperthermia after injection into the central nervous system (Snedecor and Cochran, *Statistical Methods* (Ames, Iowa: ISU Press, pp. 508–509 (1967)); Said in *Gut Hormones* (Bloom and Polak (eds.) 2nd ed., pp. 379–384, New York: Churchill-Livingston, Inc. (1981)). VIP is synthesized as a preprohormone composed of 170 amino acid residues (Cuttitta, et al., *J. Clin. Endo. Met.*, 67:576–583 (1988)). VIP, a 28 amino acid peptide with an amidated C-terminal, results from posttranslational processing (Said & Mutt, *Science*, 69:1217–1218 (1970)). The VIP peptide has been shown to contain at least two functional regions, a region involved in receptor specific binding and a region involved in biological activity (Gozes and Brenneman, *Molecular Neurobiology*, 3:201–236 (1989)).

Another biological function of VIP is as a modulatory agent in the central nervous system (CNS) and periphery (Said & Mutt, *Science*, 69:1217–1218 (1970)). In the rat brain, VIP elevates cAMP levels and stimulates adenylate cyclase in the cortex, striatum, hypothalamus, hippocampus, thalamus, and midbrain (Deschodt-Lanckman, et al., *FEBS Lett.*, 83:76–80 (1977); Etgen and Browning, *J. Neurosci.*, 3:2487–2493; Kerwin, et al., *J. Pharm. Pharmacol.*, 32:561–566 (1980); Quick, et al., *Biochem. Pharmacol.*, 27: 2209–2213 (1978)). Further, VIP fulfills several criteria for a neurotransmitter mediating penile erection. It is present in nerve fibers innervating cavernous smooth muscle and blood vessels and is elevated during erection (Ottesen, et al., *Br. Med. J.*, 288:9 (1984); Dixon, et al., *J. Endocrinol.*, 100:249 (1984)). Injection of exogenous VIP induces erection in man (Ottesen, et al., *Br. Med. J.*, 288:9 (1984)) and penile levels have been shown to be decreased in impotent men (Gu, et al., Lancet, 2:315 (1984)). Since VIP appears to be important in erection formation (Anderson, et al., *J. Physiol.*, 350:209 (1984)), its administration has been found to be helpful in relieving penile dysfunction (See, e.g., Gozes, et al., *Endocrinology*, 125(4):2945–2949; U.S. Pat. No. 5,147,855 and U.S. Pat. No. 5,217,953).

VIP is also biologically active in the mammalian lung and has been found to be colocalized to cholinergic neurons in the lung (Shimosegawa, et al., *Reg. Peptides*, 2:181 (1989)). Endogenous VIP is present in nerves supplying airway smooth muscle as well as glands and in pulmonary vessels within the normal adult lung (Ley, et al., *Cell Tissue Res.*, 220:238 (1981)). VIP functions in the lung as a bronchodilator and relaxes pulmonary vascular smooth muscles (Diamond, et al., *Am. Rev. Respir. Dis.*, 128:827–832 (1983); Greenburg, et al., *Thorax*, 40:715 (1985); Morice, et al., *Lancet*, 1:457–458 (1984)). VIP has been found to be deficit in the airways of patients with bronchial asthma (Lebacq-Verheyden, et al., *J. Cell. Biochem.*, 36:85–96 (1988)).

The actions caused by VIP may be mediated by specific receptors. VIP receptors were initially detected in the CNS using brain homogenates (Robberecht, et al., *Eur. J. Biochem.*, 90:147–154 (1978)) and, more recently, autoradiographic studies have localized the receptors to discrete brain areas such as the cerebral cortex, striatum, supraoptic nucleus of the hypothalamus, dentate gyms, pinneal and area postrema (Besson, et al., *Peptides*, 5:339–340 (1984); DeSouza, et al., *Neurosci. Lett.*, 56:113–120 (1985); Shaffer and Moody, *Peptides*, 7:283–288 (1986)). VIP receptors have also been characterized in liver membranes (Bataille, et al., *Endocrinology*, 95:713–721 (1974)) and pancreatic acinar cells (Christophe, et al., *J. Biol. Chem.*, 251:4629–4634 (1976)).

The biological actions of VIP in the lung may also be mediated by VIP receptors which have been detected in binding assays using plasma membranes derived from the rat, mouse, guinea pig, and human lung (Christophe, et al., *Peptides*, 2:253–258 (1981); Dickinson, et al., *Peptides* 7:791–800 (1986); Robberecht, et al., *Peptides*, 4:241–250 (1982)). Using in vitro autoradiographic techniques and lung slices, VIP receptors have been localized to the alveoli and epithelium of the rat lung and pulmonary artery smooth muscle and alveolar walls of the human lung (Leroux, et al., *Endocrinology*, 114:1506–1512 (1984); Leys, et al., *FEBS Lett.*, 199:198–202 (1984)). The lung VIP receptors were characterized using cross-linking techniques and found to have an apparent molecular weight of 67 KDa (Lebacq-Verheyden, et al., *Mol. Cell. Biol.*, 8:3129–3135 (1988)). Additionally, it has been demonstrated that VIP positively regulates adenylate cyclase activity in the lung (Oilerenshaw, et al., *N. Engl. J. Med.*, 320:1244–1248 (1989)).

Recently, it was determined that VIP receptors are present in the malignant lung (Shaffer, et al., *Peptides*, 8:1101–1106 (1987)). Lung cancer is a serious public health problem which kills approximately 150,000 people in the United States annually (Minna, et al., in: *Cancer: Principles and Practice of Oncology* (DeVita, et al. (eds.), pp. 507–599 (1985)). Traditionally lung cancer is treated with chemo and/or radiation therapy, but better survival rates might be possible with the development of new modes of therapy. Lung cancer can be divided into small cell lung cancer (SCLC) which accounts for approximately 25% of the lung cancer cases and non-small cell lung cancer (NSCLC). NSCLC can be further subdivided into adenocarcinoma, large cell carcinoma and squamous cell carcinoma each of which account for approximately 25% of the lung cancer cases. SCLC uses bombesin/gastrin releasing peptide (BN/GRP) as an autocrine growth factor (Cuttitta, et al., *Nature*, 316:823–825 (1985)). Thus, SCLC synthesizes and secretes BN/GRP, and BN or GRP bind to cell surface receptors and stimulate the growth of SCLC. Further, NSCLC synthesizes and secretes transforming growth factor alpha (i.e., TGF-alpha) which, in turns, binds to cell surface epidermal growth factor (EGF) receptors and stimulates NSCLC growth (Imanishi, et al., *J. Natl. Cancer Inst.*, 81:220–223 (1989)). In contrast, VIP receptors are present in cells derived from SCLC and the three other major types of lung cancer (all members of NSCLC), large cell carcinoma, squamous cell carcinoma and adenocarcinoma (Shaffer, et al., *Peptides*, 8:1101–1106 (1987)).

Recently, Gozes, et al. have developed a VIP antagonist that has proven useful for altering the function of the vasoactive intestinal peptide. (See, U.S. Pat. No. 5,217,953 issued to Gozes, et al. (1993)). This VIP antagonist was designed to retain the binding properties of VIP for its receptor, but to lack the amino acid sequence necessary for biological activity which, it is believed, requires, among other factors, a phenylalanine residue at position 6. Amino acids 1–6 of native VIP were therefore replaced by a segment of neurotensin in order to alter the biological activity of native VIP and to change the membrane permeability of the peptide. Three of the six amino acids added in the neurotensin segment are basic. This is in contrast to native VIP which, in this region, contains no basic residues and only one acidic residue. Indeed, the concept that a tetrapeptide with basic amino acids at both ends and a proline residue adjacent to the N-terminal amino acid is essential for high activity on membrane permeability has been proven correct for neurotensin and other peptides as well. As such, the VIP antagonist developed by Gozes, et al. is a hybrid molecule containing an amino acid sequence necessary for VIP receptor binding (i.e., amino acids 7–28 of VIP), and an N-terminal amino acid sequence corresponding to a portion of neurotensin.

Studies have shown that this VIP antagonist effectively antagonizes VIP-associated activity. More particularly, it has been found that this VIP antagonist inhibits the effect of VIP on the sexual behavior of a mammal. (See, e.g., Gozes, et al., *Endocrinology*, 125(4):2945–2949; and U.S. Pat. No. 5,217, 953.) It has also been found that the hybrid VIP antagonist potently inhibits VIP binding (with a higher affinity than VIP itself); attenuates VIP-stimulated cAMP accumulation; and induces neuronal cell death in tissue culture. (See, e.g., Gozes, et al., *J. Pharmacol. Exp. Ther.*, 257(8): 959–966 (1991).) Moreover, it has been found that this VIP antagonist inhibits the growth of VIP receptor bearing tumor cells such as, for example, lung tumor cells (i.e., NSCLC cells). (See, U.S. Pat. No. 5,217,953.)

Although this VIP antagonist effectively antagonizes VIP-associated activity, there still remains a need for VIP antagonists which are more potent than the VIP hybrid antagonist developed by Gozes, et al. and which are capable of discriminating between the various VIP receptors present in cells. The present invention remedies these needs by providing such antagonists.

SUMMARY OF THE INVENTION

The present invention relates to a family of polypeptides. More particularly, the present invention relates to a family of polypeptides which are antagonists of the vasoactive intestinal polypeptide (VIP), the antagonists comprising the following amino acid sequence (SEQ ID NO.:1):

$R^1$—Lys—Pro—Arg—Arg—Pro—Tyr—Thr—Asp—Asn—
Tyr—Thr—Arg—Leu—Arg—Lys—Gln—$X^1$—Ala—$X^2$—
Lys—Lys—Tyr—Leu—Asn—Ser—Ile—Leu—AsnNH—$R^2$.

In the above formula, $R^1$ and $R^2$ are independently selected and may be functional groups including, but not limited to, the following: hydrogen, $C_1$ to $C_{20}$ alkyls and $C_1$ to $C_{20}$ acyls, provided that at least one of $R^1$ or $R^2$ is hydrogen. $X^1$ and $X^2$, in the above formula, are independently selected from the group consisting of naturally occurring amino acids and amino acid mimetics, provided that $X^2$ is not methionine.

Within the scope of the above formula, certain vasoactive intestinal polypeptide antagonists are preferred, namely those in which $R^1$ is H; $R^2$ is H; $X^1$ is a norleucine residue; $X^2$ is a valine residue (hereinafter referred to as the "NL-hybrid VIP antagonist"). Equally preferred are VIP antagonists in which $R^1$ is $CH_3(CH_2)_{16}CO$—; $R^2$ is H; $X^1$ is a norleucine residue; $X^2$ is a valine residue (hereinafter referred to as the "S-NL-hybrid VIP antagonist"). Also equally preferred are VIP antagonists in which $R^1$ is $CH_3(CH_2)_{16}CO$—; $R^2$ is H; $X^1$ is a methionine residue; $X^2$ is a valine residue (hereinafter referred to as the "S-hybrid VIP antagonist"). Further equally preferred are VIP antagonists in which $R^1$ is a $C_1$ to $C_{20}$ alkyl; $R^2$ is H; $X^1$ is a norleucine residue; $X^2$ is a valine residue. It should be noted, however, that $R^1$, $R^2$, $X^1$ and $X^2$ are selected such that the VIP antagonists of the present invention have other than the following amino acid sequence (SEQ ID NO.:2):

Lys—Pro—Arg—Arg—Pro—Tyr—Thr—Asp—Asn—Tyr—
Thr—Arg—Leu—Arg—Lys—Gln—Met—Ala—Val—Lys—
Lys—Tyr—Leu—Asn—Ser—Ile—Leu—Asn.

The VIP antagonists of the present invention are relatively short in length; typically, they are no more than 28 amino acids in length. As such, it is feasible to prepare such VIP antagonists using any of a number of chemical peptide synthesis techniques well known to those of ordinary skill in the art including both solution methods and solid phase methods, with solid phase synthesis being presently preferred. Although the VIP antagonists of the present invention are preferably prepared using chemical peptide synthesis techniques such as described above, it will be understood by those of ordinary skill in the art that they can also be prepared by other means including, for example, recombinant techniques.

It is known that VIP operates via two discrete binding sites specific for the central nervous system, one associated with stimulation of cAMP formation and one with increasing neuronal survival. More particularly, studies have indicated the presence of a low affinity, adenylate cyclase-linked receptor and a low abundance, high affinity receptor which is linked to the survival promoting-activity of VIP. From both the neuronal survival assays and the VIP-induced cAMP formation assays, infra, it has now been discovered that the VIP antagonists of the present invention are able to differentiate between the cAMP-associated VIP receptor(s) and the neuronal survival-linked VIP receptor(s). More particularly, it has been found that the NL-hybrid VIP antagonist has an affinity for both the cAMP-associated VIP receptor(s) and the neuronal survival-linked VIP receptors. It has also been found that the S-hybrid VIP antagonist and the S-NL-hybrid VIP antagonist have a higher affinity for the VIP receptor which is linked to the neuronal survival promoting-activity of VIP. Due to their ability to differentiate and discriminate between the various VIP receptors, the VIP antagonists of the present invention can be used in in vivo studies to delineate the physiological functions of VIP in the CNS and its behavioral consequences.

Moreover, it has surprisingly been discovered that the VIP antagonists of the present invention inhibit VIP-associated activity to a greater extent (i.e., with greater potency) than the VIP antagonist previously developed by Gozes, et al. (i.e., the "hybrid VIP antagonist"). More particularly, it has been found that when the methionine residue at position 17 of the hybrid VIP antagonist is replaced with a norleucine residue, a VIP antagonist (i.e., the "NL-hybrid antagonist") is produced that is as much as ten-fold more potent than the original hybrid VIP antagonist at inhibiting VIP-associated activity. It has also been found that when an acyl radical (i.e., a lipophilic moiety such as, for example, a stearyl radical) is added to the N-terminal of the hybrid VIP antagonist, a VIP antagonist (i.e., the "S-hybrid antagonist") is produced that is as much as ten-fold more potent than the hybrid VIP antagonist at inhibiting VIP-associated activity. Moreover, it has been found that when the methionine residue at position 17 of the hybrid VIP antagonist is replaced with a norleucine residue and an acyl radical (i.e., a lipophilic moiety) is added to the N-terminal of the VIP antagonist, a VIP antagonist (i.e., the "S-NL-hybrid antagonist") is produced that is as much as one thousand-fold more potent than the hybrid VIP antagonist at inhibiting VIP-associated activity.

As such, the VIP antagonists of the present invention can be used to inhibit, i.e., antagonize, VIP-associated activity in a mammal. Thus, the present invention provides a method of antagonizing VIP-associated activity in a mammal, the method comprising administering to the mammal a vasoactive intestinal polypeptide (VIP) antagonist in an amount sufficient to effect the antagonism, the antagonist comprising the following amino acid sequence (SEQ ID NO.:1):

$R^1$—Lys—Pro—Arg—Arg—Pro—Tyr—Thr—Asp—Asn—
Tyr—Thr—Arg—Leu—Arg—Lys—Gln—$X^1$—Ala—$X^2$—
Lys—Lys—Tyr—Leu—Asn—Ser—Ile—Leu—AsnNH—$R^2$.

The discussions pertaining to $R^1$, $R^2$, $X^1$ and $X^2$, both supra and infra, are fully applicable to the VIP antagonists used in this method of the present invention and, thus, such discussions will not be repeated at this time.

More particularly, in one aspect, the present invention provides a method of inhibiting the growth of VIP receptor containing tumor cells, the method comprising contacting the tumor cells with a vasoactive intestinal polypeptide (VIP) antagonist in an amount sufficient to effect inhibition, the antagonist comprising the following amino acid sequence (SEQ ID NO.:1):

$R^1$—Lys—Pro—Arg—Arg—Pro—Tyr—Thr—Asp—Asn—
Tyr—Thr—Arg—Leu—Arg—Lys—Gln—$X^1$—Ala—$X^2$—
Lys—Lys—Tyr—Leu—Asn—Ser—Ile—Leu—AsnNH—$R^2$.

The discussions pertaining to $R^1$, $R^2$, $X^1$ and $X^2$, both supra and infra, are fully applicable to the VIP antagonists used in this method of the present invention and, thus, such discussions will not be repeated at this time. It should be noted, however, within the scope of the above method, certain vasoactive intestinal polypeptide antagonists are preferred, namely those in which $R^1$ is H; $R^2$ is H; $X^1$ is a norleucine residue; $X^2$ is a valine residue. Equally preferred are VIP antagonists in which $R^1$ is $CH_3(CH_2)_{16}CO$—; $R^2$ is H; $X^1$ is a norleucine residue; $X^2$ is a valine residue.

In yet another aspect, the present invention provides a method of inducing neuronal cell death, the method comprising contacting neuronal cells with a vasoactive intestinal polypeptide (VIP) antagonist in an amount sufficient to effect the death of the neuronal cells, the antagonist comprising the following amino acid sequence (SEQ ID NO.:1):

$R^1$—Lys—Pro—Arg—Arg—Pro—Tyr—Thr—Asp—Asn—
Tyr—Thr—Arg—Leu—Arg—Lys—Gln—$X^1$—Ala—$X^2$—
Lys—Lys—Tyr—Leu—Asn—Ser—Ile—Leu—AsnNH—$R^2$.

The discussions pertaining to $R^1$, $R^2$, $X^1$ and $X^2$, both supra and infra, are fully applicable to the VIP antagonists used in this method of the present invention and, thus, such discussions will not be repeated at this time. It should be noted, however, that within the scope of the above method, certain vasoactive intestinal polypeptide antagonists are preferred, namely those in which $R^1$ is H; $R^2$ is H; $X^1$ is a norleucine residue; $X^2$ is a valine residue. Equally preferred are VIP antagonists in which $R^1$ is $CH_3(CH_2)_{16}CO$—; $R^2$ is H; $X^1$ is a norleucine residue; $X^2$ is a valine residue. Also equally preferred are VIP antagonists in which $R^1$ is $CH_3(CH_2)_{16}CO$—; $R^2$ is H; $X^1$ is a methionine residue; $X^2$ is a valine residue.

In a further aspect, the present invention provides a method of inhibiting VIP-induced cAMP formation in a mammal, the method comprising administering to the mammal a vasoactive intestinal polypeptide (VIP) antagonist in an amount sufficient to effect inhibition, the antagonist comprising the following amino acid sequence (SEQ ID NO.:1):

$R^1$—Lys—Pro—Arg—Arg—Pro—Tyr—Thr—Asp—Asn—
Tyr—Thr—Arg—Leu—Arg—Lys—Gln—$X^1$—Ala—$X^2$—
Lys—Lys—Tyr—Leu—Asn—Ser—Ile—Leu—AsnNH—$R^2$.

The discussions pertaining to $R^1$, $R^2$, $X^1$ and $X^2$, both supra and infra, are fully applicable to the VIP antagonists used in this method of the present invention and, thus, such discussions will not be repeated at this time. It should be noted, however, within the scope of the above method, certain vasoactive intestinal polypeptide antagonists are preferred, namely those VIP antagonists in which $R^1$ is H; $R^2$ is H; $X^1$ is a norleucine residue; $X^2$ is a valine residue.

In yet another aspect, the present invention provides a method of inhibiting circadian rhythm in a mammal, the method comprising administering to the mammal a vasoactive intestinal polypeptide (VIP) antagonist in an amount sufficient to effect inhibition, the antagonist comprising the following amino acid sequence (SEQ ID NO.:1):

$R^1$—Lys—Pro—Arg—Arg—Pro—Tyr—Thr—Asp—Asn—
Tyr—Thr—Arg—Leu—Arg—Lys—Gln—$X^1$—Ala—$X^2$—
Lys—Lys—Tyr—Leu—Asn—Ser—Ile—Leu—AsnNH—$R^2$.

The discussions pertaining to $R^1$, $R^2$, $X^1$ and $X^2$, both supra and infra, are fully applicable to the VIP antagonists used in this method of the present invention and, thus, such discussions will not be repeated at this time. It should be noted, however, that within the scope of the above method, certain vasoactive intestinal polypeptide antagonists are preferred, namely those in which $R^1$ is H; $R^2$ is H; $X^1$ is a norleucine residue; $X^2$ is a valine residue. Equally preferred are VIP antagonists in which $R^1$ is $CH_3(CH_2)_{16}CO$—; $R^2$ is H; $X^1$ is a methionine residue; $X^2$ is a valine residue.

In yet a further aspect, the present invention provides a method of inhibiting neuroblastoma cell division, the method comprising contacting the neuroblastoma cells with a vasoactive intestinal polypeptide (VIP) antagonist in an amount sufficient to effect the inhibition, the antagonist comprising the following amino acid sequence (SEQ ID NO.:1):

$R^1$—Lys—Pro—Arg—Arg—Pro—Tyr—Thr—Asp—Asn—
Tyr—Thr—Arg—Leu—Arg—Lys—Gln—$X^1$—Ala—$X^2$—
Lys—Lys—Tyr—Leu—Asn—Ser—Ile—Leu—AsnNH—$R^2$.

The discussions pertaining to $R^1$, $R^2$, $X^1$ and $X^2$, both supra and infra, are fully applicable to the VIP antagonists used in this method of the present invention and, thus, such discussions will not be repeated at this time. It should be noted, however, that within the scope of the above method, certain vasoactive intestinal polypeptide antagonists are preferred, namely those in which $R^1$ is H; $R^2$ is H; $X^1$ is a norleucine residue; $X^2$ is a valine residue. Equally preferred are VIP antagonists in which $R^1$ is H; $R^2$ is H; $X^1$ is a methionine residue; $X^2$ is a valine residue. Also equally preferred are VIP antagonists in which $R^1$ is $CH_3(CH_2)_{16}CO$—; $R^2$ is H; $X^1$ is a methionine residue; $X^2$ is a valine residue.

Finally, the present invention provides pharmaceutical compositions comprising one of the previously described VIP antagonists in an amount sufficient to inhibit VIP associated activity, and a pharmaceutically acceptable diluent, carrier or excipient. Such compositions can be used to effectively inhibit VIP-associated activity and function in a mammal.

Other advantages, objects, features and embodiments of the present invention will become apparent from the description which follows.

For mitogenic assays, human NM cells were seeded in 35 mm diameter tissue culture dishes (CORNING) at a density of 0.2×10$^6$ cells per dish in RPMI-1640 medium plus 10% fetal calf serum. One day after seeding, VIP was introduced into the culture medium. Cell counts were performed with a hemocytometer, using trypan blue staining for viability, on the second day (24 hours) after the VIP treatment. Results shown on the graph are cell/dish×1000. Error bars represent the standard error. Three-six replicates were counted for each data point and experiments were repeated three independent times. $EC_{50}=5\times10^{-7}$M.

Figure 5:
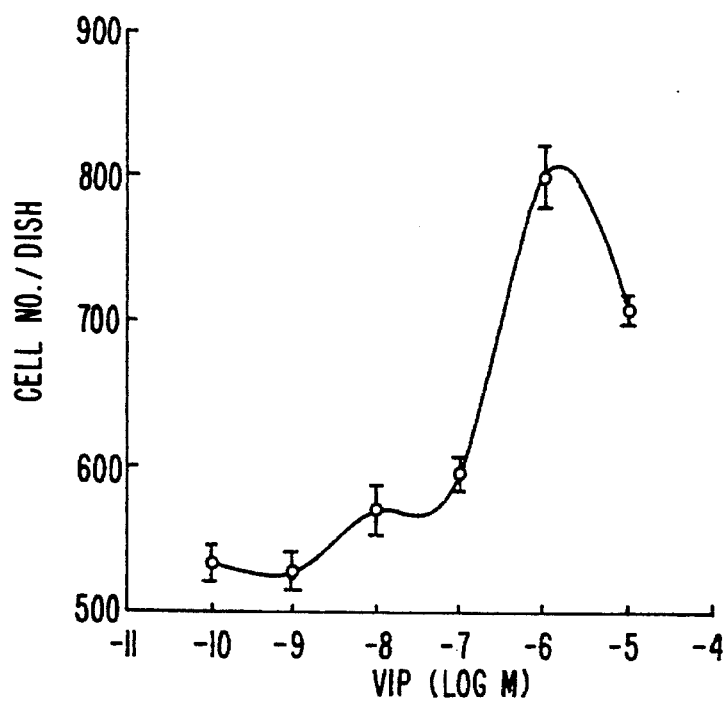
FIG. 5. VIP increases neuroblastoma (NMB) cell division (measured by cell counts). Neuroblastoma (NMB) cells have been grown in culture using RPMI-1640 medium supplemented with 10% fetal calf serum and gentamicin (100 μl of 40 mg/ml stock solution per 100 mL medium) in a humidified atmosphere of 5% $CO_2$, 95% air. Cells were harvested with Puck's saline containing 0.25% trypsin and 0.02M EDTA every four days, centrifuged and seeded in 60 mm diameter tissue culture dishes (CORNING) at a density of 0.6–0.7×10$^6$ cells per dish.
Figure 6:
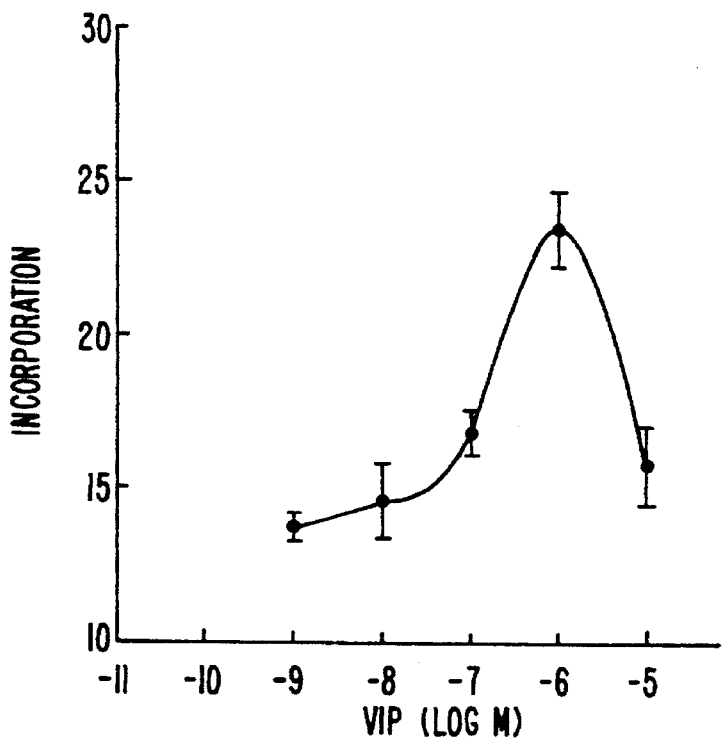

FIG. 6. VIP increases thymidine incorporation into neuroblastoma cells. Cells were grown as described in FIG. 5. One day after seeding, the cells were exposed to both $^3$H-thymidine (4 μCi/dish) and VIP for a 24 hours incubation period. Medium was then removed and 0.2N NaOH was added to the 35 mm tissue culture dishes (0.5 mL/dish) and incubated for about 20 min. The cell suspension was filtered through GF/C filter paper pre-soaked with 0.3% polyethylenimine. Filters were washed with 25 mL $H_2O$ and 5 mL ethanol, dried and counted for radioactivity. Experiments were repeated three times with as many as 10 replicates per data point, per experiment. Error bars represent the standard error. Results (incorporation) shown on the graph are CPM× 10$^5$. $EC_{50}=5\times10^{-7}$M.

Figure 7:
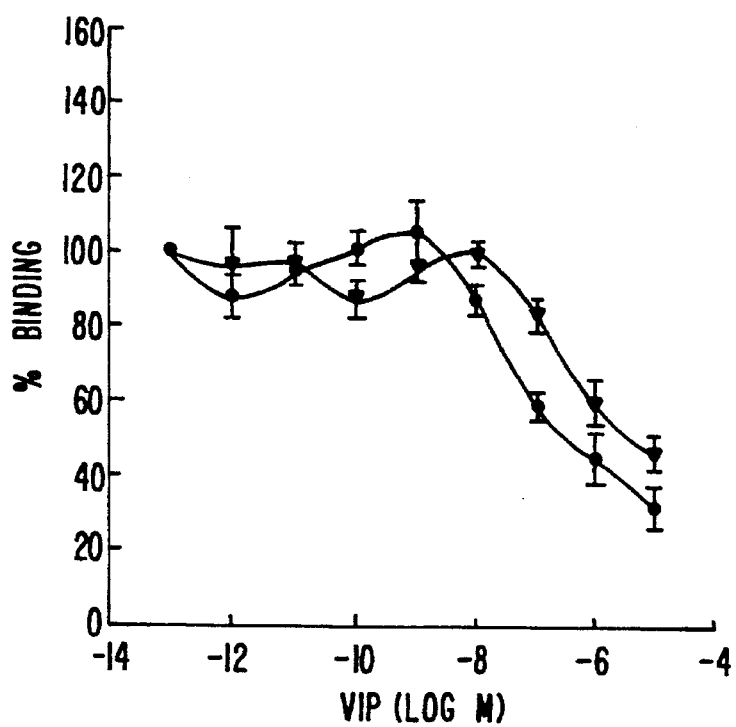

FIG. 7. VIP receptors on neuroblastoma (NMB) cells. VIP binding and displacement experiments were conducted on intact cells at 4° C. using phosphate buffered saline (PBS) containing 0.1% bovine serum albumin. Previous work indicated that a short term exposure to VIP resulted in an internalization of the peptide receptor complex into clear endosomal vesicles, with a half time in minutes (Gozes, et al., supra, (1991); Rosselin, et al., supra, (1988)). VIP was degraded in lysosomes or might serve as an intracellular effector. Most VIP receptors were recycled to the cell surface. The internalization was tissue specific, and was blocked at 4° C. Therefore, all binding studies were conducted at 4° C. on intact cells. Time course experiments indicated that equilibrium binding was achieved during one hour of incubation with 50 pM $^{125}$I-labeled VIP in the cell cultures (0.3 mg protein/35 mm tissue culture dish).

The labeled ligand was $^{125}$I-VIP at the tyr-22 (2000 Ci/mmol, Amersham Corp., Arlington Heights, Ill.), or iodinated VIP labeled at tyr$^{10}$ as well as tyr$^{22}$, with a similar specific activity, purchased from NEN (Boston, Mass.). Alternatively, the VIP was iodinated according to the procedure described by Werner, et al. (*Biochem. Biophys. Res. Commun.*, 133:228–232 (1985)). Cells were incubated with the tested peptide (10 μM-1 pM) for 30 min prior to the addition of 50 pM $^{125}$I-VIP (Gozes, et al., supra, (1991)). Labeled ligand was incubated with the cultures for one hour; the media was then removed and cells were washed three times by the addition and rapid removal of 1 mL PBS (at 4° C.). The labeled cells were then dissolved in 0.2N NaOH and transferred for radioactivity counting. Experiments were repeated at least three times, each containing triplicates, error bars represent the standard error. Cells were grown for 24 hours (circles) and 48 hours (triangles). Earlier time points (22 hours after plating) displayed identical results to those obtained 24 hours after plating, earlier than that the cells are still round (do not adhere properly to the tissue culture plates) and binding cannot be performed in the same manner. The binding parameters were determined by ACCUFIT program, Lundon-2 competition analysis (LUNDON software Inc., Chargin Falls, Ohio, U.S.A.). The curve fitting analysis indicated a single site best fit, and a $K_d$ of 0.2 μM for cells grown for 24 hours and a $K_d$ of 2 μM for cells grown for 48 hours. The calculated $B_{max}$ was 6×10$^{-14}$ moles/mg and 1.5×10$^{-14}$ moles/mg for cells grown for 24 hours as compared to cells grown for 48 hours, respectively.

Figure 8:
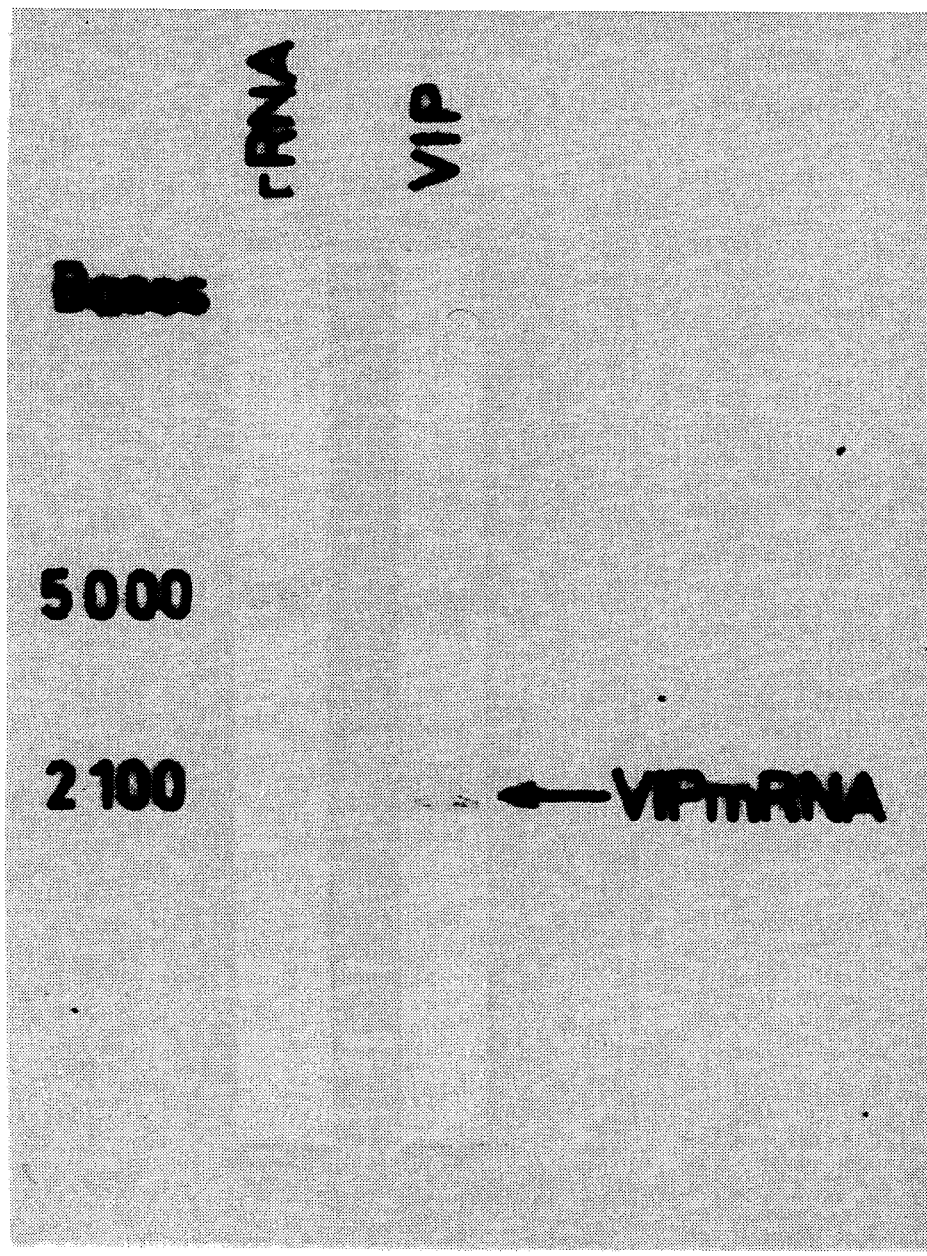

FIG. 8. Identification of VIP mRNA in neuroblastoma cells. Total RNA was prepared from NMB cells, 24 hours after plating, using the RNAsol method (Cinna/Biotex Labs. International Inc., Friendswood, Tex.). RNA was then subjected to agarose gel electrophoresis and Northern blot hybridization, using the human VIP-exon specific riboprobe ($^{32}$P-UTP labeled, as before (Gozes, supra, (1987)). The resulting autoradiogram is shown. As a control, blots were washed for three, 15 minutes periods in a boiling solution containing 0.1% SDS, 75 mM NaCl, 7.5 mM NaCitrate and rehybridized with 28S rRNA oligo nucleotide probe as before (Burbu, et al., *Nucleic Acid Res.*, 17:7115 (1989)).

Figure 9:
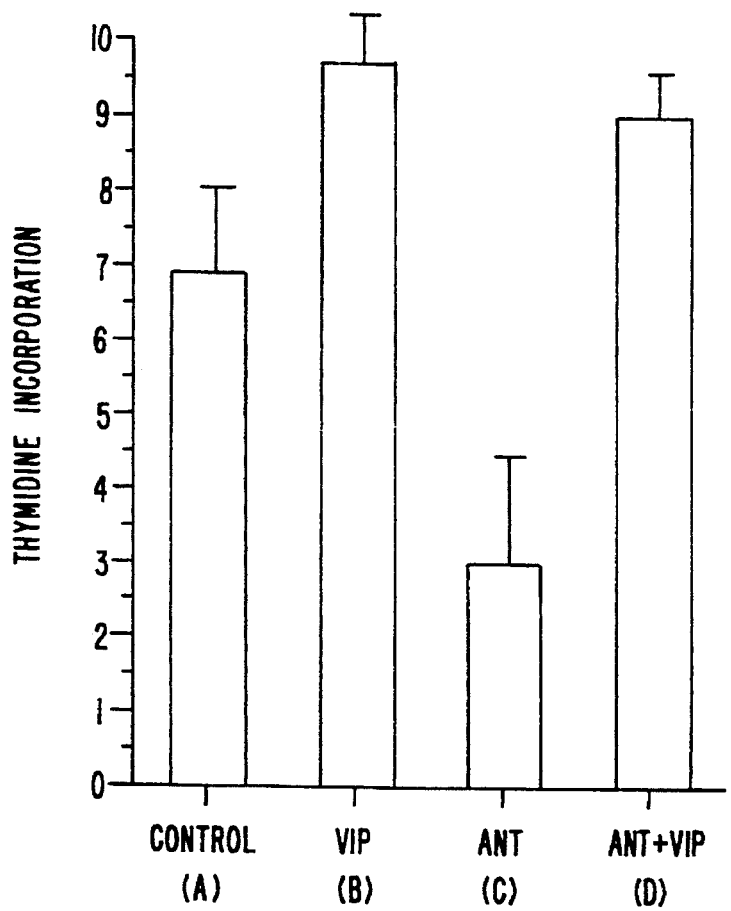

FIG. 9. The hybrid VIP antagonist inhibits VIP-induced neuroblastoma cell division. (A) Control; (B) 1 µM VIP; (C) 10 µM hybrid VIP antagonist; and (D) 1 µM VIP and 10 µM hybrid VIP antagonist. Neuroblastoma cells were grown as described in FIG. 5, and thymidine incorporation was measured as described in FIG. 6.

Figure 10:
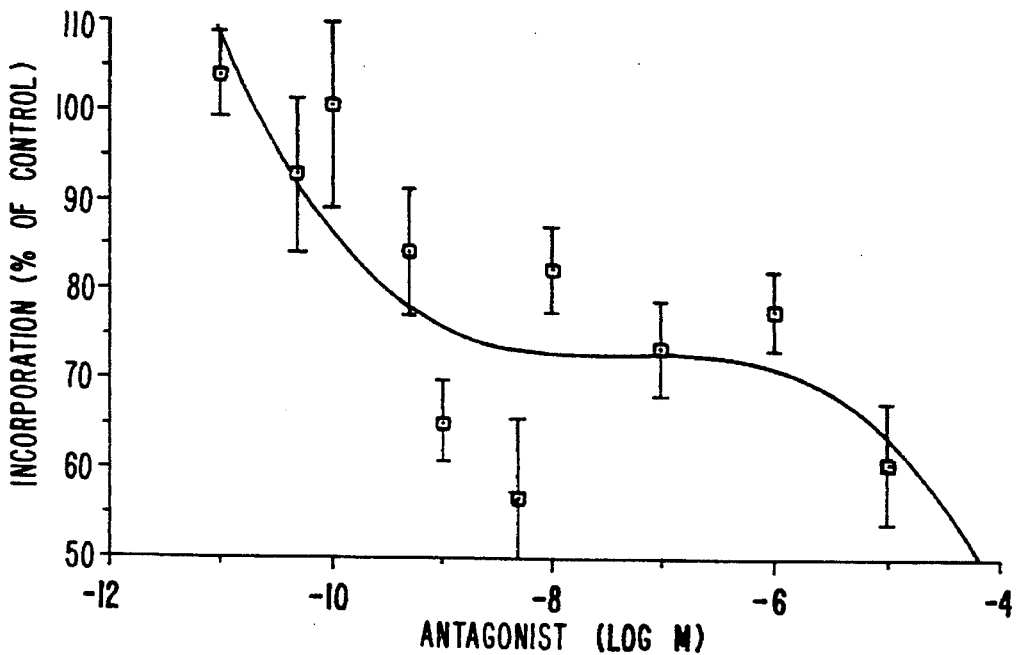

FIG. 10. The hybrid VIP antagonist inhibits VIP-induced neuroblastoma cell division in a dose dependent manner. The same experiment as that described in FIG. 6 for VIP is now conducted with the hybrid VIP antagonist; the only modification is that in this experiment more thymidine was initially added.

DEFINITIONS

"Peptides," "polypeptides" and "oligopeptides" are chains of amino acids (typically L-amino acids) whose α carbons are linked through peptide bonds formed by a condensation reaction between the carboxyl group of the α carbon of one amino acid and the amino group of the α carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free α-amino group on the amino acid at the amino terminal of the peptide or to the α-amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide or to the carboxyl group of an amino acid at any other location within the peptide.

Typically, the amino acids making up a polypeptide are numbered in order, starting at the amino terminal and increasing in the direction of the carboxy terminal of the polypeptide. Thus, when one amino acid is said to "follow" another, that amino acid is positioned closer to the carboxy terminal of the polypeptide than the "preceding" amino acid.

The term "residue" as used herein refers to an amino acid or an amino acid mimetic that is incorporated into a peptide by an amide bond or an amide bond mimetic. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

The term "biologically active" refers to a peptide sequence that will interact with naturally occurring biological molecules to either activate or inhibit the function of those molecules in vitro or in vivo. The term "biologically active" is most commonly used herein to refer to vasoactive intestinal polypeptide (VIP) antagonists that inactivate or inhibit VIP-associated activity both in vitro or in vivo.

The phrase "consisting essentially of" is used herein to exclude any elements that would substantially alter the essential properties of the VIP antagonists to which the phrase refers. Thus, the description of a polypeptide "consisting essentially of . . . " excludes any amino acid substitutions, additions, or deletions that would substantially alter the biological activity of that polypeptide.

The term "contacting" is used herein interchangeably with the following: combined with, added to, mixed with, passed over, incubated with, flowed over, etc. Moreover, the VIP antagonists of the present invention may be "administered" by any conventional method such as, for example, parenteral, oral, topical, and inhalation routes.

"An amount sufficient" or "an effective amount" is that amount of a given VIP antagonist which antagonizes or inhibits the VIP-associated activity of interest or, which provides either a subjective relief of a symptom(s) or an objectively identifiable improvement as noted by the clinician or other qualified observer. The dosing range varies with the VIP antagonist used, the VIP-associated activity to be antagonized, the route of administration and the potency of the particular antagonist.

The term "specifically bind(s)" refers to the binding of a VIP antagonist to a particular molecule and to no other molecule to which the antagonist is normally exposed to during the course of its activity.

The term "neuroblastoma" refers to a sarcoma of nervous system origin, composed chiefly of neuroblasts and affecting mostly infants and children up to 10 years of age. Most of such tumors arise in the autonomic nervous system (sympathico-blasroma) or in the adrenal medulla.

The term "circadian rhythm" refers to the basic rhythm with a periodicity of approximately 24 hours that organisms undergo when isolated from the daily rhythmical changes of the environment, for example, when kept entirely in the dark. This rhythm demonstrates the ability of the organs to measure time.

The term "diurnal rhythm" refers to a pattern of activity based on a 24-hour cycle, in which there are regular light and dark periods.

The term "biological clock" or "internal clock" refer to an internal mechanism by which many plants and animals keep a sense of time, making possible a rhythmic pattern of behavior. Many organisms have such clocks producing activity cycles of approximately 24 hours (circadian rhythm) which, however, can be affected by external influences that set the clock (e.g., entrainment). Biological clocks affect not only whole organism activities, such as sleeping, but also cellular patterns of activity, such as varying metabolic rates.

The amino acids referred to herein are described by shorthand designations as follows:

TABLE I

Amino Acid Nomenclature

| Name | 3-letter | 1 letter |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |

TABLE I-continued

Amino Acid Nomenclature

| Name | 3-letter | 1 letter |
|---|---|---|
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S—Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

DETAILED DESCRIPTION OF THE INVENTION AND PREFERRED EMBODIMENTS

In one aspect, the present invention provides vasoactive intestinal polypeptide (VIP) antagonists, the antagonists comprising the following amino acid sequence (SEQ ID NO.:1):

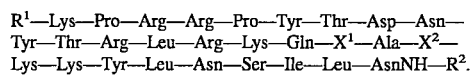

$R^1$—Lys—Pro—Arg—Arg—Pro—Tyr—Thr—Asp—Asn—Tyr—Thr—Arg—Leu—Arg—Lys—Gln—$X^1$—Ala—$X^2$—Lys—Lys—Tyr—Leu—Asn—Ser—Ile—Leu—AsnNH—$R^2$.

In the above formula, $R^1$ and $R^2$ are independently selected and may be functional groups including, but not limited to, the following: hydrogen, $C_1$ to $C_{20}$ alkyls and $C_1$ to $C_{20}$ acyls, provided that at least one of $R^1$ or $R^2$ is hydrogen. The term "independently selected" is used herein to indicate that the two R groups, $R^1$ and $R^2$, may be identical or different (e.g., both $R^1$ and $R^2$ may be hydrogen or, $R^1$ may be a $C_{16}$ acyl radical and $R^2$ may be hydrogen, etc.). The term "alkyl" is used herein to refer to substituents that are monovalent aliphatic hydrocarbon radicals. The alkyl groups may be straight-chain or branched-chain, with straight-chain alkyl groups (i.e., $C_1$ to $C_{20}$) being preferred. Examples of suitable alkyl radicals include, but are not limited to, the following: methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and icosyl.

The term "acyl" is used herein to refer to an organic radical derived from an organic acid by removal of the hydroxyl group. For example, the acyl radical or group "butyryl" is derived from butanoic acid by removal of the hydroxyl group. Similarly, the acyl group "stearyl" is derived from stearic acid by removal of the hydroxyl group. In accordance with the present invention, the acyl group may be saturated or unsaturated, with acyl groups having from one to twenty carbon atoms (i.e., $C_1$ to $C_{20}$) being preferred. A "saturated" acyl group is one which has no double or triple bonds, whereas an "unsaturated" acyl group is one which has double or triple bonds. Suitable acyl groups include, but are not limited to, the following: butyryl, hexanoyl, octanoyl, lauryl, myristyl, palmityl, stearyl, aracidyl, linoceryl, etc. In addition to the foregoing, it will be readily apparent to those of ordinary skill in the art that a large number of other acyl groups can be derived from various organic acids by removal of the hydroxyl group.

$X^1$ and $X^2$, in the above formula, are independently selected from the group consisting of naturally occurring amino acids and amino acid mimetics, provided that $X^2$ is not methionine. The term "independently selected" is used herein to indicate that the two X groups, $X^1$ and $X^2$, may be identical or different (e.g., both $X^1$ and $X^2$ may be valine, etc.). $X^1$ and $X^2$, as previously mentioned, may be either a naturally occurring amino acid or a known analog of a natural amino acid that functions in a manner similar to the naturally occurring amino acids (i.e., an amino acid mimetic). Suitable amino acids that can be used to form the antagonists of the present invention include, but are not limited to, those listed in Table I, supra.

Within the scope of the above formula, certain vasoactive intestinal polypeptide antagonists are preferred, namely those in which $R^1$ is H; $R^2$ is H; $X^1$ is a norleucine residue; $X^2$ is a valine residue. Equally preferred are VIP antagonists in which $R^1$ is $CH_3(CH_2)_{16}CO$—; $R^2$ is H; $X^1$ is a norleucine residue; and $X^2$ is a valine residue. Also equally preferred are VIP antagonists in which $R^1$ is $CH_3(CH_2)_{16}CO$—; $R^2$ is H; $X^1$ is a methionine residue; and $X^2$ is a valine residue. Further equally preferred are VIP antagonists in which $R^1$ is a $C_1$ to $C_{20}$ alkyl; $R^2$ is H; $X^1$ is a norleucine residue; and $X^2$ is a valine residue. In addition, other preferred VIP antagonists are those in which $X^1$ and $X^2$ are amino acids arid amino acid mimetics of hydrophopbic character. Such amino acids include, but are not limited to, leucine, norleucine, phenylalanine and valine (e.g., $X^1$ is leucine, valine or phenylalanine, and $X^2$ is leucine, norleucine or phenylalanine). It should be noted, however, that $R^1$, $R^2$, $X^1$ and $X^2$ are selected such that the VIP antagonists of the present invention have other than the following composition (SEQ ID NO.:2):

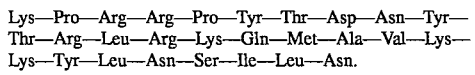

Lys—Pro—Arg—Arg—Pro—Tyr—Thr—Asp—Asn—Tyr—Thr—Arg—Leu—Arg—Lys—Gln—Met—Ala—Val—Lys—Lys—Tyr—Leu—Asn—Ser—Ile—Leu—Asn.

In addition, it will be readily apparent to those of ordinary skill in the art that the VIP antagonists of the present invention may be subject to various changes, such as insertions, deletions, and substitutions, either conservative or non-conservative, where such changes might provide for certain advantages in their use, i.e., to increase biological activity. By conservative substitutions is meant replacing an amino acid residue with another which is biologically and/or chemically similar, e.g., one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Residues which can be modified without loosing the biological activity of the VIP antagonist can be identified by single amino acid substitutions, deletions, or insertions using conventional techniques known to those of ordinary skill in the art, this especially true of the VIP antagonists of the present invention being that they are relatively short in length. In addition, the contributions made by the side chains of the residues can be probed via a systematic scan with a specified amino acid (e.g., Ala).

The VIP antagonists of the present invention are relatively short in length and are typically no more than 28 amino acids in length. As such, it is feasible to prepare such VIP antagonists using any of a number of chemical peptide synthesis techniques well known to those of ordinary skill in the art including both solution methods and solid phase methods, with solid phase synthesis being presently preferred.

In particular, solid phase synthesis in which the C-terminal amino acid of the peptide sequence is attached to an insoluble support followed by sequential addition of the remaining amino acids in the sequence is the preferred method for preparing the VIP antagonists of the present invention. Techniques for solid phase synthesis are described by Barany and Merrifield, *Solid-Phase Peptide Synthesis*, in *The Peptides: Analysis, Synthesis, Biology* (Gross and Meienhofer (eds.), Academic press, New York, vol. 2, pp. 3–284 (1980)); Merrifield, et al., *J. Am. Chem. Soc.* 85, 2149–2156 (1963); and Stewart, et al., *Solid Phase Peptide Synthesis* (2nd ed., Pierce Chem. Co., Rockford, Ill. (1984)), the teachings of which are hereby incorporated by reference.

Solid phase synthesis is started from the carboxy-terminal end (i.e., the C-terminus) of the peptide by coupling a protected amino acid via its carboxyl group to a suitable solid support. The solid support used is not a critical feature of the present invention provided that it is capable of binding to the carboxyl group while remaining substantially inert to the reagents utilized in the peptide synthesis procedure. For example, a starting material can be prepared by attaching an amino-protected amino acid via a benzyl ester linkage to a chloromethylated resin or a hydroxymethyl resin or via an amide bond to a benzhydrylamine (BHA) resin or p-methylbenzhydrylamine (MBHA) resin. Materials suitable for us as solid supports are well known to those of skill in the art and include, but are not limited to, the following: halomethyl resins, such as chloromethyl resin or bromomethyl resin; hydroxymethyl resins; phenol resins, such as 4-($\alpha$-[2,4-dimethoxyphenyl]-Fmoc-aminomethyl)phenoxy resin; tert-alkyloxycarbonyl-hydrazidated resins, and the like. Such resins are commercially available and their methods of preparation are known by those of ordinary skill in the art.

The acid form of the peptides of the present invention may be prepared by the solid phase peptide synthesis procedure using a benzyl ester resin as a solid support. The corresponding amides may be produced by using benzhydrylamine or methylbenzhydrylamine resin as the solid support. Those skilled in the art will recognize that when the BHA or MBHA resin is used, treatment with anhydrous hydrofluoric acid to cleave the polypeptide from the solid support produces a polypeptide having a terminal amide group.

The $\alpha$-amino group of each amino acid used in the synthesis should be protected during the coupling reaction to prevent side reactions involving the reactive $\alpha$-amino function. Certain amino acids also contain reactive side-chain functional groups (e.g. sulfhydryl, amino, carboxyl, hydroxyl, etc.) which must also be protected with appropriate protecting groups to prevent chemical reactions from occurring at those sites during the polypeptide synthesis. Protecting groups are well known to those of skill in the art. See, for example, *The Peptides: Analysis, Synthesis, Biology, Vol. 3: Protection of Functional Groups in Peptide Synthesis* (Gross and Meienhofer (eds.), Academic Press, New York (1981)), the teachings of which are incorporated herein by reference.

A properly selected $\alpha$-amino protecting group will render the $\alpha$-amino function inert during the coupling reaction, will be readily removable after coupling under conditions that will not remove side chain protecting groups, will not alter the structure of the peptide fragment, and will prevent racemization upon activation immediately prior to coupling. Similarly, side-chain protecting groups must be chosen to render the side chain functional group inert during the synthesis, must be stable under the conditions used to remove the $\alpha$-amino protecting group, and must be removable after completion of the polypeptide synthesis under conditions that will not alter the structure of the polypeptide.

Illustrative examples of protecting groups for an $\alpha$-amino group include, but are not limited to, the following: aromatic urethane-type groups such as, for example, fluorenylmethyloxycarbonyl (Fmoc), carbobenzoxy (Cbz), and substituted benzyloxycarbonyls including p-chlorobenzyloxycarbonyl, o-chlorobenzyloxycarbonyl, 2,4-dichlorobenzyloxycarbonyl, 2,6-dichlorobenzyloxycarbonyl, etc.; aliphatic urethane-type groups such as, for example, butyloxycarbonyl (Boc), t-amyloxycarbonyl, isopropyloxycarbonyl, 2-(p-biphenylyl)-isopropyloxycarbonyl, allyloxycarbonyl, etc.; and cycloalkyl urethane-type groups such as, for example, cyclopentyloxycarbonyl, cyclohexyloxycarbonyl, cycloheptyloxy-carbonyl, adamantyloxycarbonyl (Adoc), etc. In a presently preferred embodiment, fluorenylmethyloxycarbonyl (Fmoc) is the $\alpha$-amino protecting group used.

For the side chain amino group present in lysine (Lys), any of the protecting groups described above for the protection of the $\alpha$-amino group are suitable. Moreover, other suitable protecting groups include, but are not limited to, the following: butyloxycarbonyl (Boc), p-chlorobenzyloxycarbonyl, p-bromobenzyloxycarbonyl, o-chlorobenzyloxycarbonyl, 2,6-dichlorobenzyloxycarbonyl, 2,4-dichlorobenzyloxycarbonyl, o-bromobenzyloxycarbonyl, p-nitrobenzyloxycarbonyl, t-butyloxycarbonyl, isopropyloxycarbonyl, t-amyloxycarbonyl, cyclopentyloxycarbonyl, cyclohexyloxycarbonyl, cycloheptyloxycarbonyl, adamantyloxycarbonyl, p-toluenesulfonyl, etc. In a presently preferred embodiment, the side chain amino protecting group for Lys is butyloxycarbonyl (Boc).

For protection of the guanidino group of arginine (Arg), examples of suitable protecting groups include, but are not limited to, the following: nitro, tosyl (Tos), carbobenzoxy (Cbz), adamantyloxycarbonyl (Adoc), butyloxycarbonyl (Boc), 4-methoxy-2,3,6-trimethylbenzenesulfonyl (Mtr) and 2,2,5,7,8-pentamethylchloroman-6-sulfonyl (PMC). In a presently preferred embodiment, 4-methoxy-2,3,6-trimethylbenzenesulfonyl and 2,2,5,7,8-pentamethylchloroman-6-sulfonyl are the protecting group used for Arg.

The hydroxyl group on the side chains of serine (Ser), threonine (Thr) or tyrosine (Tyr) can be protected by a $C_1$–$C_4$ alkyl such as, for example, methyl, ethyl and t-butyl, or by a substituted benzyl such as, for example, p-methoxybenzyl, p-nitrobenzyl, p-chlorobenzyl, o-chlorobenzyl and 2,6-dichlorobenzyl. The preferred aliphatic hydroxyl protecting group for Ser, Thr and Tyr is t-butyl.

The carboxyl group of aspartic acid (Asp) may be protected by, for example, esterification using groups such as benzyl, t-butyl, cyclohexyl, cyclopentyl, and the like. For Asp, t-butyl is the presently preferred protecting group.

The basic imidazole ring in histidine (His) may be protected by, for example, t-butoxymethyl (Bom), butyloxycarbonyl (Boc) and fluorenylmethyloxycarbonyl (Fmoc). In a preferred embodiment, t-butoxymethyl (Bom) is the protecting group used.

Coupling of the amino acids may be accomplished by a variety of chemistries known to those of skill in the art. Typical approaches involve either the conversion of the amino acid to a derivative that will render the carboxyl group more susceptible to reaction with the free N-terminal amino group of the polypeptide fragment, or use of a suitable coupling agent such as, for example, N,N'-dicyclohexylcarbodiimide (DCC) or N,N'-diisopropylcarbodiimide (DIPCDI). Frequently, hydroxybenzotriazole (HOBt) is employed as a catalyst in these coupling reactions. Appropriate synthesis chemistries are disclosed in *The Peptides: Analysis, Structure, Biology, Vol. 1: Methods of Peptide Bond Formation* (Gross and Meienhofer (eds.), Academic Press, New York (1979)); and Izumiya, et al., *Synthesis of Peptides* (Maruzen Publishing Co., Ltd., (1975)), both of which are incorporated herein by reference.

Generally, synthesis of the polypeptide is commenced by first coupling the C-terminal amino acid, which is protected at the Nα-amino position by a protecting group such as fluorenylmethyloxycarbonyl (Fmoc), to a solid support. Prior to coupling of Fmoc-Asn, the Fmoc residue has to be removed from the polymer. Fmoc-Asn can, for example, be coupled to the 4-(α-[2,4-dimethoxyphenyl]-Fmoc-aminomethyl)phenoxy resin using N,Nα-dicyclohexylcarbodimide (DCC) and hydroxybenzotriazole (HOBt) at about 25° C. for about two hours with stirring. Following the coupling of the Fmoc-protected amino acid to the resin support, the α-amino protecting group is removed using 20% piperidine in DMF at room temperature.

After removal of the α-amino protecting group, the remaining Fmoc-protected amino acids are coupled stepwise in the desired order. Appropriately protected amino acids are commercially available from a number of suppliers (e.g., Nova (Switzerland) or Bachera (California)). As an alternative to the stepwise addition of individual amino acids, appropriately protected peptide fragments consisting of more than one amino acid may also be coupled to the "growing" polypeptide. Selection of an appropriate coupling reagent, as explained above, is well known to those of skill in the art. It should be noted that since the VIP antagonists of the present invention are relative short in length, this latter approach (i.e., the segment condensation method) is not the most efficient method of peptide synthesis.

Each protected amino acid or amino acid sequence is introduced into the solid phase reactor in excess and the coupling is carried out in a medium of dimethylformamide (DMF), methylene chloride ($CH_2Cl_2$) or, mixtures thereof. If coupling is incomplete, the coupling reaction may be repeated before deprotection of the Nα-amino group and addition of the next amino acid. Coupling efficiency may be monitored by a number of means well known to those of skill in the art. A preferred method of monitoring coupling efficiency is by the ninhydrin reaction. Polypeptide synthesis reactions may be performed automatically using a number of commercially available peptide synthesizers (e.g., Biosearch 9500, Biosearch, San Raphael, Calif.).

The peptide can be cleaved and the protecting groups removed by stirring the insoluble carrier or solid support in anhydrous, liquid hydrogen fluoride (HF) in the presence of anisole and dimethylsulfide at about 0° C. for about 20 to 90 minutes, preferably 60 minutes; by bubbling hydrogen bromide (HBr) continuously through a 1 mg/10 mL suspension of the resin in trifluoroacetic acid (TFA) for 60 to 360 minutes at about room temperature, depending on the protecting groups selected; or, by incubating the solid support inside the reaction column used for the solid phase synthesis with 90% trifluoroacetic acid, 5% water and 5% triethylsilane for about 30 to 60 minutes. Other deprotection methods well known to those of skill in the art may also be used.

The polypeptides, i.e., VIP antagonists, of the present invention can be isolated and purified from the reaction mixture by means of peptide purification well known to those of skill in the art. For example, the polypeptides may be purified using known chromatographic procedures such as reverse phase HPLC, gel permeation, ion exchange, size exclusion, affinity, partition, or countercurrent distribution. See, the Example Section, infra, for a detailed description of the methods and protocols used to synthesize and purify the VIP antagonists of the present invention.

Although the VIP antagonists of the present invention are preferably prepared or produced using chemical peptide synthesis techniques such as described above, it will be understood by those of ordinary skill in the art that they can also be prepared by other means including, for example, recombinant techniques.

In another aspect, the present invention provides a method of antagonizing VIP-associated activity in a mammal, the method comprising administering to the mammal a vasoactive intestinal polypeptide (VIP) antagonist in an amount sufficient to effect the antagonism, the antagonist comprising the following amino acid sequence (SEQ ID NO.:1):

$R^1$—Lys—Pro—Arg—Arg—Pro—Tyr—Thr—Asp—Asn—
Tyr—Thr—Arg—Leu—Arg—Lys—Gln—$X^1$—Ala—$X^2$—
Lys—Lys—Tyr—Leu—Asn—Ser—Ile—Leu—AsnNH—$R^2$.

In the above formula, $R^1$ and $R^2$ are independently selected and may be functional groups including, but not limited to, the following: hydrogen, $C_1$ to $C_{20}$ alkyls and $C_1$ to $C_{20}$ acyls, provided that at least one of $R^1$ or $R^2$ is hydrogen. The term "independently selected" is used herein to indicate that the two R groups, $R^1$ and $R^2$, may be identical or different (e.g., both $R^1$ and $R^2$ may be hydrogen). The term "alkyl" is used herein to refer to substituents that are monovalent aliphatic hydrocarbon radicals. The alkyl groups may be straight-chain or branched-chain, with straight-chain alkyl groups (i.e., $C_1$ to $C_{20}$) being preferred. The term "acyl" is used herein to refer to an organic radical derived from an organic acid by removal of the hydroxyl group. For example, the acyl radical or group "butyryl" is derived from butanoic acid by removal of the hydroxyl group. Similarly, the acyl group "stearyl" is derived from stearic acid by removal of the hydroxyl group. In accordance with the present invention, the acyl group may be saturated or unsaturated, with acyl groups having from one to twenty carbon atoms (i.e., $C_1$ to $C_{20}$) being preferred. A "saturated" acyl group is one which has no double or triple bonds, whereas an "unsaturated" acyl group is one which has double or triple bonds. Suitable acyl groups include, but are not limited to, the following: butyryl, hexanoyl, octanoyl, lauryl, myristyl, palmityl, stearyl, aracidyl, linoceryl, etc. In addition to the foregoing, it will be readily apparent to those of ordinary skill in the art that a large number of other acyl groups can be derived from various organic acids by removal of the hydroxyl group.

$X^1$ and $X^2$, in the above formula, are independently selected from the group consisting of naturally occurring amino acids and amino acid mimetics, provided that $X^2$ is not methionine. The term "independently selected" is used herein to indicate that the two X groups, $X^1$ and $X^2$, may be identical or different (e.g., both $X^1$ and $X^2$ may be valine, etc.). $X^1$ and $X^2$, as previously mentioned, may be either a naturally occurring amino acid or a known analog of a natural amino acid that functions in a manner similar to the naturally occurring amino acids (i.e., an amino acid mimetic). Suitable amino acids that can be used to form the antagonists of the present invention include, but are not limited to, those listed in Table I, supra.

Within the scope of the above method, certain vasoactive intestinal polypeptide antagonists are preferred, namely those in which $R^1$ is H; $R^2$ is H; $X^1$ is a norleucine residue; $X^2$ is a valine residue. Equally preferred are VIP antagonists in which $R^1$ is $CH_3(CH_2)_{16}CO$—; $R^2$ is H; $X^1$ is a norleucine residue; and $X^2$ is a valine residue. Also equally preferred are VIP antagonists in which $R^1$ is $CH_3(CH_2)_{16}CO$—; $R^2$ is H; $X^1$ is a methionine residue; and $X^2$ is a valine residue. Further equally preferred are VIP antagonists in which $R^1$ is a $C_1$ to $C_{20}$ alkyl; $R^2$ is H; $X^1$ is a norleucine residue; and $X^2$ is a valine residue. In addition, other preferred VIP antagonists are those in which $X^1$ and $X^2$ are amino acids and amino acid mimetics of hydrophopbic character. Such amino acids include, but are not limited to, leucine, norleucine, phenylalanine and valine (e.g., $X^1$ is leucine, valine or phenylalanine, and $X^2$ is leucine, norleucine or phenylalanine). It should be noted that $R^1$, $R^2$, $X^1$ and $X^2$ of the VIP antagonist used in the above method are selected such that the VIP antagonist has other than the following composition (SEQ ID NO.:2):

Lys—Pro—Arg—Arg—Pro—Tyr—Thr—Asp—Asn—Tyr—
 Thr—Arg—Leu—Arg—Lys—Gln—Met—Ala—Val—Lys—
 Lys—Tyr—Leu—Asn—Ser—Ile—Leu—Asn.

In addition, it will be readily apparent to those of ordinary skill in the art that the VIP antagonists of the present invention may be subject to various changes, such as insertions, deletions, and substitutions, either conservative or non-conservative, where such changes might provide for certain advantages in their use, i.e., to increase biological activity. By conservative substitutions is meant replacing an amino acid residue with another which is biologically and/or chemically similar, e.g., one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Residues which can be modified without loosing the biological activity of the VIP antagonist can be identified by single amino acid substitutions, deletions, or insertions using conventional techniques known to those of ordinary skill in the art, this especially true of the VIP antagonists of the present invention being that they are relatively short in length. In addition, the contributions made by the side chains of the residues can be probed via a systematic scan with a specified amino acid (e.g., Ala).

As previously mentioned, the VIP antagonists of the present invention can be used to inhibit, i.e., antagonize, VIP-associated activity and function. More particularly, the VIP antagonists of the present invention can be used to inhibit the growth of VIP receptor containing tumor cells; to induce neuronal cell death; to inhibit VIP-induced cAMP formation or accumulation; to inhibit circadian rhythm in a mammal; and to inhibit neuroblastoma growth (i.e., cell division), etc. Each of the various methods of using the VIP antagonists of the present invention to inhibit VIP-associated activity/function will be explained in greater detail hereinbelow. From these examples, it will be understood by those of ordinary skill in the art that the VIP antagonists of the present invention can be used in a similar manner to inhibit a large number of other VIP-associated activities.

As such, in one aspect, the present invention provides a method of inhibiting the growth of VIP receptor containing tumor cells, the method comprising contacting the tumor cells with a vasoactive intestinal polypeptide (VIP) antagonist in an amount sufficient to effect inhibition, the antagonist comprising the following amino acid sequence (SEQ ID NO.:1):

$R^1$—Lys—Pro—Arg—Arg—Pro—Tyr—Thr—Asp—Asn—
 Tyr—Thr—Arg—Leu—Arg—Lys—Gln—$X^1$—Ala—$X^2$—
 Lys—Lys—Tyr—Leu—Asn—Ser—Ile—Leu—AsnNH—$R^2$.

The previous discussion pertaining to $R^1$, $R^2$, $X^1$ and $X^2$ is fully applicable to the VIP antagonists used in this method of the present invention and, thus, it will not be repeated again with respect to this particular method. It should be noted, however, that $R^1$, $R^2$, $X^1$ and $X^2$ of the VIP antagonists used in the above method are selected such that the VIP antagonists have other than the following composition (SEQ ID NO.:2):

Lys—Pro—Arg—Arg—Pro—Tyr—Thr—Asp—Asn—Tyr—
 Thr—Arg—Leu—Arg—Lys—Gln—Met—Ala—Val—Lys—
 Lys—Tyr—Leu—Asn—Ser—Ile—Leu—Asn.

Moreover, within the scope of the above method, certain vasoactive intestinal polypeptide antagonists are preferred, namely those in which $R^1$ is H; $R^2$ is H; $X^1$ is a norleucine residue; $X^2$ is a valine residue. Equally preferred are VIP antagonists in which $R^1$ is $CH_3(CH_2)_{16}CO$—; $R^2$ is H; $X^1$ is a norleucine residue; and $X^2$ is a valine residue.

In order for the VIP antagonists of the present invention to exhibit antagonistic activity, they must be capable of binding to the VIP receptor without activating it. Thus, in order to evaluate the antagonistic activity of a given VIP antagonist, it is desirable to assay both for binding affinity and for the ability of the antagonist to inactivate the bound receptor.

Means of assaying for the binding affinity of a particular ligand (i.e., a VIP antagonist) for a cell-surface protein (i.e., a VIP receptor) are well known to those of ordinary skill in the art. In typical binding assays, the putative antagonist is immobilized and exposed to a labeled receptor or, alternatively, an immobilized receptor is exposed to a labeled ligand or antagonist. The immobilized moiety is then washed to remove any unbound material and the label is detected. The amount of immobilized label is proportional to the degree of binding between the receptor and the putative antagonist.

In a preferred embodiment, VIP receptor containing cells are isolated and bound to a solid support (e.g., a polyvinylchloride plate, Dynatch, Arlington, Va.). The antagonist, labeled either radioactively (e.g., with $^{125}I$) or fluorescently (e.g., with fluorescein or rhodamine), is exposed to the bound VIP receptor containing cells. After washing, the cells are isolated and the amount of bound antagonist is determined by measuring the radioactivity in, for example, a scintillation counter.

Binding is either determined directly or in competition with the native VIP. In a direct determination, the VIP antagonist is labeled, and the amount of bound VIP antagonist is directly measured. When the assay is performed as a competitive inhibition, native VIP is labeled. The VIP receptor containing cells are then exposed to the labeled ligand in the presence of varying amounts of the unlabeled VIP antagonist. When the VIP antagonist has a high affinity for the VIP receptor, it will out-compete the native VIP, resulting in a reduction of binding by the native VIP.

Figure 2:
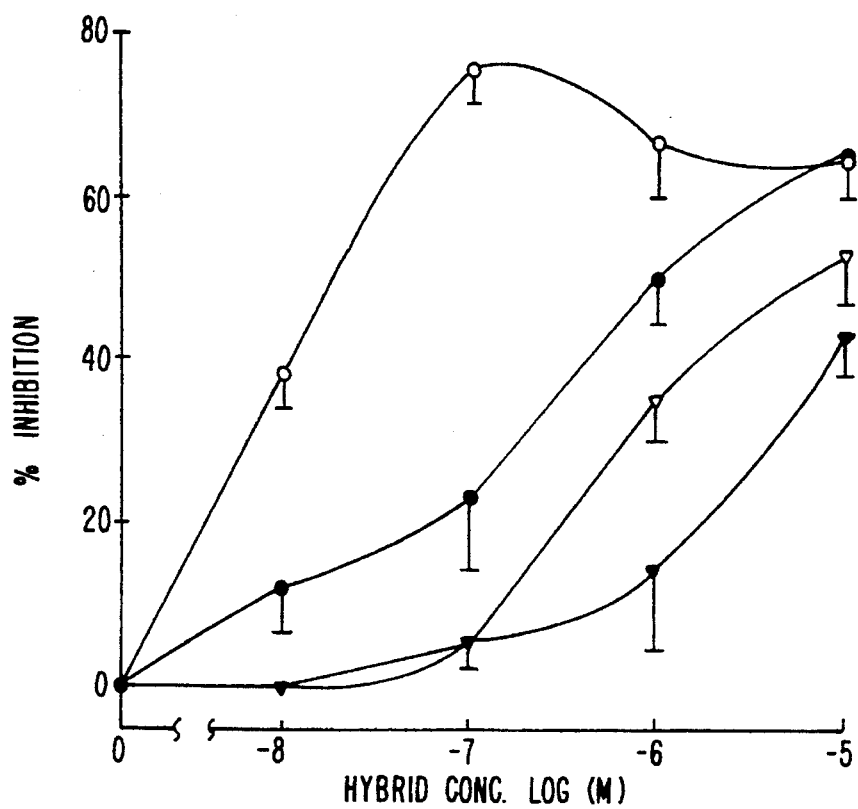
FIG. 2. VIP-stimulated cAMP formation was inhibited in the presence of the family of VIP antagonists. Cortical astrocyte cultures were incubated for 10 min with 1 μm VIP and cAMP accumulation was determined by radioimmunoassay (Gozes, et al., *J. Pharmacol. & Exp. Therap.*, 257:959 (1991)). Increasing concentrations of the antagonists were placed in the astrocyte cultures 5 minutes prior to the addition of VIP. Astrocytes were maintained in 35 mm tissue culture dishes with 0.3 mg protein per dish. Each value is the mean of 8–10 determinations from 4 experiments. The same analogues compared in FIG. 1 are compared here. The error bar is the SEM.
Figure 3:
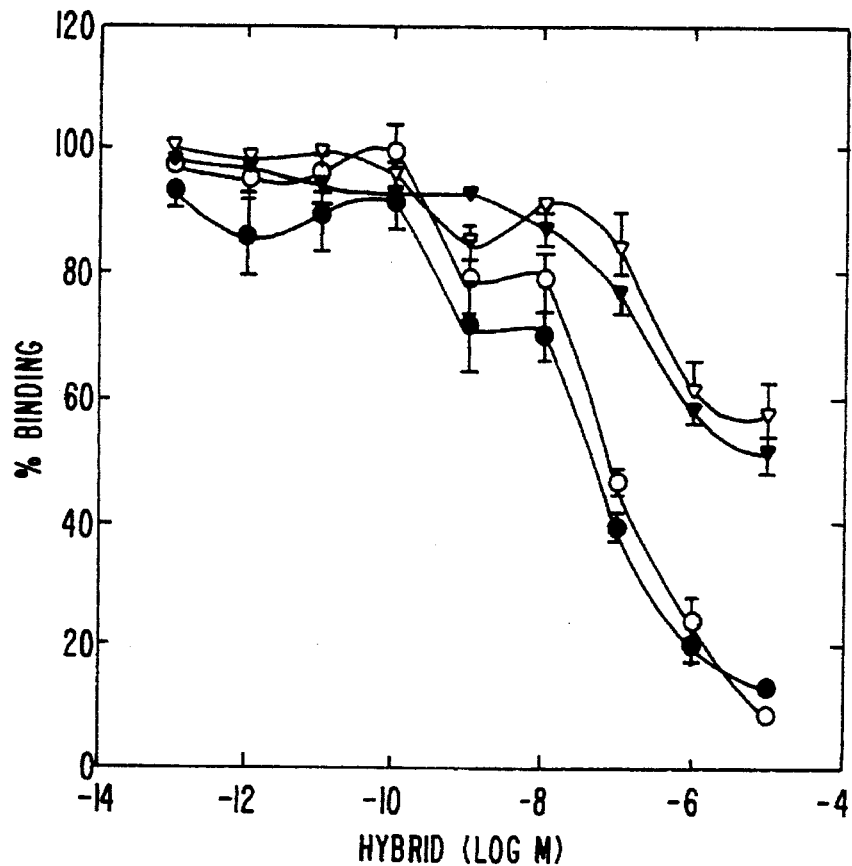
FIG. 3. Comparison of the binding capacity of the various VIP antagonists via displacement of radiolabeled $^{125}$I-VIP from astroglia cells. The same analogues compared in FIG. 1 are compared here, i.e., Hybrid antagonist (open circles), NL-hybrid antagonist (closed circles), S-hybrid antagonist (open triangles), S-NL-hybrid antagonist (closed triangles).

As such, the interactions between the antagonists of the present invention and VIP receptors were investigated in VIP binding studies conducted on VIP receptor containing tumor cells. The results of such studies are set forth in FIG. 3 and in Table II, infra, and they reveal that the S-hybrid antagonist and the S-NL-hybfid antagonist are 6-fold and 25-fold more potent than the hybrid antagonist at inhibiting $^{125}I$-VIP binding to the VIP receptors present in NSCLC cells (e.g., NCI-H838 cells). More complex results were obtained when the VIP antagonists were compared in the central nervous system, wherein it was found that the stearyl-antagonists (i.e., the S-hybrid VIP antagonist and the S-NL-hybrid VIP antagonist) have a lower affinity for the cAMP (low affinity) VIP receptor (see, FIGS. 2 and 3 and the discussion, infra), and a higher affinity for the VIP-neuronal survival associated receptor (see, FIG. 1 and the discussion, infra).

TABLE II

Potency of the VIP Antagonists

| VIP Antagonists | IC$_{50}$[a], nM |
|---|---|
| Hybrid VIP Antagonist | 3000 |
| S-Hybrid VIP Antagonist | 500 |
| S-NL-Hybrid VIP Antagonist | 200 |

[a]IC$_{50}$ is the mean concentration required to half maximally inhibit $^{125}$I-VIP binding to NCI-H383 cells.

Moreover, naturally occurring VIP is a potent mitogen in a number of cells. For example, the VIP receptor is detectable on a large variety of cell types (e.g., NSCLC), and it has been found to respond to VIP by the enhancement of cell proliferation. Carpenter, *Ann. Rev. Biochem.*, 56:881–914 (1987). Thus, the antagonistic activity of the VIP antagonists of the present invention can be determined simply by measuring the ability of the antagonist to inactivate cells bearing the appropriate VIP receptors. Means of measuring activation or, alternatively, inactivation are well known to those of skill in the art.

In a preferred embodiment, activation or, alternatively, inactivation will be measured by determining the rate of tritiated thymidine uptake by the exposed cells. Metabolically active cells will incoporate a greater amount of thymidine and, thus, present a stronger signal. Alternatively, the mitogenic activity of the VIP antagonists may be assayed by measuring the effects of the antagonist on the growth rate of a particular target cell. Methods of conducting cell growth studies are well known to those of ordinary skill in the art. See, for example, Cohen and Carpenter, *Proc. Natl. Acad. Sci. (U.S.A.)*, 72:1317–1321 (1975). Briefly, an assay of this sort requires establishing a culture of a cell line bearing the appropriate VIP receptor(s). The cells are cultured for an appropriate period of time either in the presence or absence of the putative VIP antagonist. Cell counts are taken periodically by any of a number of means well known to those of skill in the art (e.g., subsampling and manual counting or automated counting via a coulter counter, etc.). Relative mitogenic activity may be determined by a comparison of the rate of cell proliferation or, by a comparison of the final cell count in cultures containing the antagonist with cell cultures without the antagonist.

With respect to inhibiting the growth of VIP receptor containing tumor cells such as lung tumor cells (e.g., NSCLC), it has been discovered that the VIP antagonists of the present invention effectively inhibit the growth of such cells. Moreover, it has surprisingly been discovered that the VIP antagonists of the present invention inhibit the growth of VIP receptor containing tumor cells to a greater extent (i.e., with greater potency) than the VIP antagonist previously developed by Gozes, et al. (hereinafter referred to as the "hybrid VIP antagonist"). More particularly, it has been found that when the methionine residue at position 17 of the hybrid VIP antagonist is replaced with a norleucine residue, a VIP antagonist (hereinafter referred to as the "NL-hybrid antagonist") is produced that is ten-fold more potent than the VIP hybrid antagonist at inhibiting the growth of VIP receptor containing tumor cells.

The effects of the hybrid antagonist and the NL-hybrid antagonist on colony formation of non-small cell lung cancer (NSCLC) were compared, and it was found that the NL-hybrid antagonist is ten-fold more potent than the original hybrid antagonist in inhibiting cell growth (i.e., cell division) in two out of three NSCLC cell lines studies. The results set forth in Table II, infra, reveal that VIP stimulates (2–3 fold) NSCLC colony formation in agar, which is an index of cell growth. The original VIP hybrid antagonist inhibits about 50% of cell growth in cell lines NCI-H1299 and NCI-H226, and about 98% of cell growth in cell line NCI-H727. In contrast, using the same concentration of antagonist, the NL-hybrid antagonist inhibits 100% of cell growth in cell line NCI-H129, 92% of cell growth in cell line NCI-H226 and 88% of cell growth in cell line NCI-H727.

TABLE III

Effect of VIP Antagonists on NSCLC Colony Formation

| | CELL LINE | | |
|---|---|---|---|
| ADDITION | NCI-H1299 | NCI-H727 | NCI-H226 |
| None (control) | 29 ± 3.1 | 35.2 ± 2.3 | 43.1 ± 5.7 |
| 1 µM VIP | 55.8 ± 19.8 | 115 ± 22.7 | 87.4 ± 4.8 |
| 1 µM Hybrid-Antagonist | 14.3 ± 4.0 | 0.7 ± 0.9 | 20.0 ± 6.7 |
| 1 µM NL-Hybrid-Antagonist | 0 | 4.2 ± 3.1 | 3.5 ± 2.5 |

In addition, the ability of VIP and the S-hybrid VIP antagonist to stimulate c-fos mRNA was examined; c-fos mRNA is a marker for cancer cell proliferation. In doing so, it was found that VIP stimulates c-los mRNA. In contrast, the presence of the VIP antagonist effectively inhibits c-los mRNA. This is true regardless of whether the VIP antagonist is co-administered with VIP or added by itself (See, Table IV, infra).

TABLE IV

Ability to Stimulate c-fos mRNA

| Addition | c-fos mRNA[a] |
|---|---|
| NONE | 1.0 |
| VIP, 10 nM | 5.6 |
| VIP + S-Hybrid VIP Antagonist, 1 µM | 0.7 |
| S-Hybrid VIP Antagonist, 1 µM | 0.8 |

[a]NCI-H810 cells were treated with the peptide and the c-fos mRNA determined after 1 hour.

As such, it is readily apparent that by contacting the VIP receptor containing tumor cells with one of the VIP antagonists of the present invention (e.g., the NL-hybrid VIP antagonist), one can effectively inhibit, i.e., antagonize, the growth of VIP receptor containing tumor cells (e.g., NSCLC, SCLC, etc.).

In yet another aspect, the present invention provides a method of inducing neuronal cell death, the method comprising contacting neuronal cells with a vasoactive intestinal polypeptide (VIP) antagonist in an amount sufficient to effect the death of the neuronal cells, the antagonist comprising the following amino acid sequence (SEQ ID NO.:1):

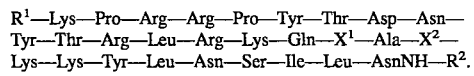

The previous discussion pertaining to R$^1$, R$^2$, X$^1$ and X$^2$ is fully applicable to the VIP antagonists used in this method of the present invention and, thus, it will not be repeated again with respect to this particular method. It should be noted, however, that R$^1$, R$^2$, X$^1$ and X$^2$ of the VIP antagonists used in the above method are selected such that the VIP antagonists have other than the following composition (SEQ ID NO.:2):

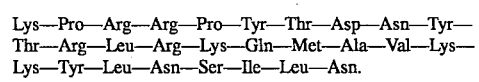

Moreover, within the scope of the above method, certain vasoactive intestinal polypeptide antagonists are preferred, namely those in which R$^1$ is H; R$^2$ is H; X$^1$ is a norleucine residue; $X^2$ is a valine residue. Equally preferred are VIP antagonists in which $R^1$ is $CH_3(CH_2)_{16}CO—$; $R^2$ is H; $X^1$ is a norleucine residue; and $X^2$ is a valine residue. Also equally preferred are VIP antagonists in which $R^1$ is $CH_3(CH_2)_{16}CO—$; $R^2$ is H; $X^1$ is a methionine residue; $X^2$ is a valine residue.

For assays of neuronal cell functions, namely the effects of the VIP antagonists on neuronal survival, a number or different assays can be used including, for example, cell culture assays, organ culture assays, whole embryo ex vivo and in vivo assays. These various assays can be used to assess general metabolic activities, neuronal-specific activities (such as, for example, synthesis and breakdown of neurotransmitters), electrophysiological functions, cell morphology and survival. In vivo assays provide an additional behavioral aspect. VIP has previously been assessed using all of the aforementioned assays (see, e.g., Gozes and Brenneman, *Molec. Neurobiol.*, 3:1 (1989); Gozes and Brenneman, *J. Molec. Neurosci.*, 4:1 (1993) and Gressens, et al., *Nature*, 362:155 (1993)).

To assess the effects of the VIP anatagonists on neuronal survival, for example, dissociated mouse spinal cord cultures (obtained from 12-day-old embryos) were employed using previously described methods (see, for example, Brenneman et al., *Dev. Brain Res.*, 9:13 (1983); Brenneman, et al., *Dev. Brain Res.*, 15:211 (1984); Brenneman, et al., *Peptide*, 6(2):35 (1985); Brenneman, et al., *J. Pharmacol. Exp. Therap.*, 233:402 (1985)). Briefly, cells were plated in 10% horse serum, 10% fetal calf serum in MEM. One day after plating, the medium was changed to 5% horse serum supplemented with defined medium components. After nine days in vitro, the cultures were given a change of medium and treated with the VIP anatagonists in the absence of tetrodotoxin. The duration of treatment was from day 9 to day 14, after which the cultures were fixed for immunocytochemistry tor NSE (neuron specific enolase, a well defined neuronal marker). Cell counts were performed on 100 fields, with a total area of 50 mm². Neurons were counted without knowledge of type of treatment.

With respect to inducing neuronal cell death, it has surprisingly been discovered that the VIP antagonists of the present invention induce neuronal cell death to a greater extent (i.e., with greater potency) than the VIP antagonist previously developed by Gozes, et al. (i.e., the "hybrid VIP antagonist"). More particularly, it has been found that when the methionine residue at position 17 of the hybrid VIP antagonist is replaced with a norleucine residue, a VIP antagonist (hereinafter referred to as the "NL-hybrid antagonist") is produced that is ten-fold more potent than the original hybrid VIP antagonist at inducing neuronal cell death. Using the NL-hybrid VIP antagonist, maximal effect was observed at $10^{-10}$M, while 10-fold more antagonist was needed to achieve a similar effect when the hybrid VIP antagonist was used (See, FIG. 1). Thus, by changing a single amino acid, a 10-fold increase in biological activity in the central nervous system is achieved.

It has also been found that when an acyl radical (i.e., a lipophilic moiety such as, for example, a stearyl radical) is added to the N-terminal of the hybrid VIP antagonist, a VIP antagonist (hereinafter referred to as the "S-hybrid antagonist") is produced that is ten-fold more potent at inducing neuronal cell death than the hybrid VIP antagonist. Thus, it was found that the S-hybrid VIP antagonist is similar to the NL-hybrid antagonist in terms of its ability to induce neuronal cell death (See, FIG. 1).

Figure 1:
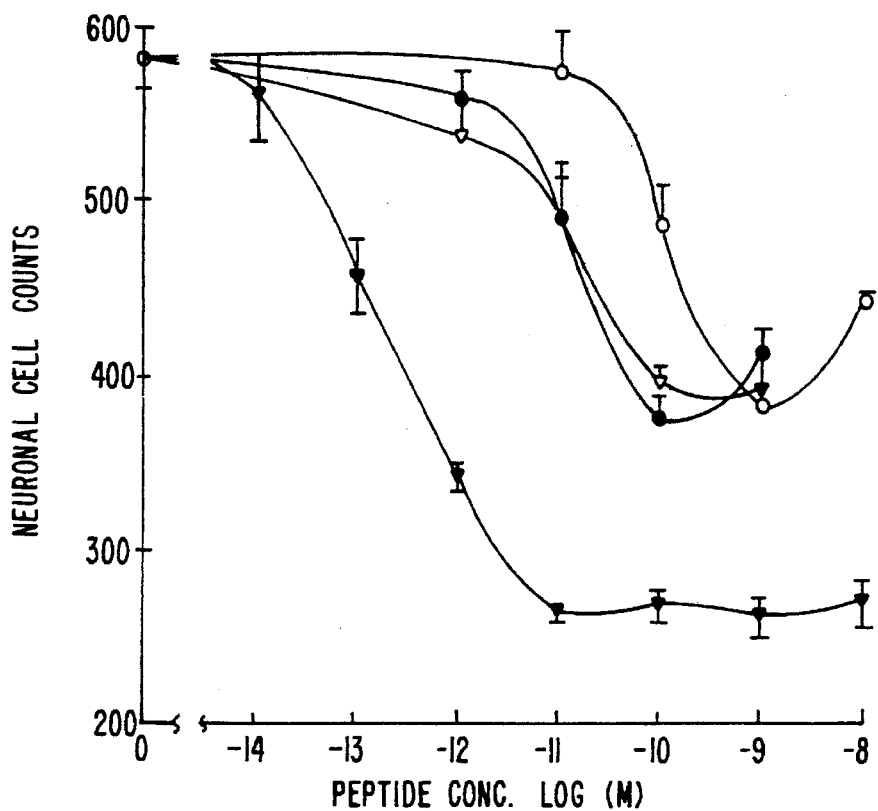
FIG. 1. Neuronal survival was reduced in spinal cord cultures treated with a family of VIP-neurotensin hybrid antagonists. Hybrid antagonist (open circles), NL-hybrid antagonist (closed circles), S-hybrid antagonist (open triangles), S-NL-hybrid antagonist (closed triangles) were added to dissociated spinal cord cells nine days after plating. The duration of treatment was 9 days with no changes of media. At the conclusion of the treatment period, neurons were identified immunocytochemically with antisera to neuron specific enolase. The immuno-positive cells (neurons) were counted in 100 fields of 0.5 mm$^2$ each. Each value is the mean or 4 dishes. The error bar is the SEN. Significant decreases from control were observed at all concentrations or antagonists $\geq 10^{-10}$M (P<0.01).

Moreover, it has been found that when the methionine residue at position 17 of the hybrid VIP antagonist is replaced with a norleucine residue and an acyl radical (i.e., a lipophilic moiety) is added to the N-terminal of the VIP antagonist, a VIP antagonist (hereinafter referred to as "S-NL-hybrid antagonist") is produced that is one hundred-fold more potent than the hybrid VIP antagonist at inducing neuronal cell death (See, FIG. 1). Thus, a combination of the two alterations (i.e., the norleucine residue at position 17 and an acyl radical at the N-terminus) results in a molecule that is a 100-fold more potent and more efficacious in neuronal killing than the original hybrid VIP antagonist developed by Gozes, et al., supra.

In a further aspect, the present invention provides a method of inhibiting VIP-induced cAMP formation in a mammal, the method comprising administering to the mammal a vasoactive intestinal polypeptide (VIP) antagonist in an amount sufficient to effect inhibition, the antagonist comprising the following amino acid sequence (SEQ ID NO.:1):

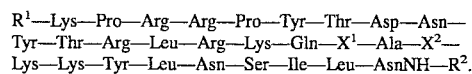

The previous discussion pertaining to $R^1$, $R^2$, $X^1$ and $X^2$ is fully applicable to the VIP antagonists used in this method of the present invention and, thus, it will not be repeated again with respect to this particular method. It should be noted, however, that $R^1$, $R^2$, $X^1$ and $X^2$ of the VIP antagonists used in the above method are selected such that the VIP antagonists have other than the following composition (SEQ ID NO.:2):

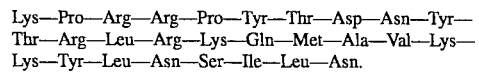

Moreover, within the scope of the above method, certain vasoactive intestinal polypeptide antagonists are preferred, namely those VIP antagonists in which $R^1$ is H; $R^2$ is H; $X^1$ is a norleucine residue; $X^2$ is a valine residue.

VIP-stimulated adenylate cyclase activity has been observed in various areas of the central nervous system (Quik, et al., *Biochem. Pharmacol.*, 27:2209–2213 (1978); and Deschodt-Lanckman, et al., *FEBS Lett.*, 93:76–80 (1977). VIP has been found to produce significant increases in cAMP levels in a variety of tissues including, for example, reproductive and brain tissue (Said, "Vasoactive Intestinal Peptide," *Advances in Peptide Hormone Series* (Raven Press, New York (1982)); Magistrotti, et al., *Nature*, 308:280 (1984); Carmena, et al., *Biochem. Biophys. Acta.* 763:414 (1983)). Moreover, the hybrid VIP antagonist previously developed by Gozes, et al. has been found to inhibit, i.e., decrease, the accumulation of cyclic AMP (i.e., cAMP) in VIP-stimulated glia cells (Gozes, et al., *J. Pharmacol. & Exp. Therap.*, 257:959 (1991)).

In view of the foregoing, astroglia cells were utilized to compare the effects the VIP antagonists of the present invention have on VIP-stimulated cAMP formation. For cAMP determinations, the general protocols involve either the measurement of adenylate cyclase activity or, the use of radioimmunoassays for cAMP which utilize a cAMP determination kit from NEN (New England Nuclear, Boston, Mass.)36 previously described by Gozes, et al. (*J. Pharmacol. Exp. Therap.*, 257:959 (1991)). An HCl (0.05M) extract neutralizecl with 0.5M NaOH may be utilized for the tests.

In comparing the various VIP antagonists, it was found that the NL-hybrid VIP antagonist, like the hybrid VIP antagonist, effectively inhibits VIP-induced cAMP formation. In contrast, it was found that the S-hybrid VIP antagonist and the S-NL-hybrid VIP antagonist do not effectively inhibit VIP-induced cAMP formation. In fact, it was found that the S-NL-VIP antagonist is 100-fold less potent in inhibiting VIP-induced cAMP formation than the hybrid VIP antagonist or the NL-hybrid VIP antagonist (see, FIG. 2).

Moreover, it is known that VIP operates via two discrete binding sites specific for the central nervous system, one associated with stimulation of cAMP formation and one with increasing neuronal survival. More particularly, studies have indicated the presence of a low affinity, adenylate cyclase-linked receptor and a low abundance, high affinity receptor which is linked to the survival promoting-activity of VIP. This survival-promoting activity is associated with both a secretagogue activity of VIP as well as a mitogenic activity.

From both the neuronal survival assays and the VIP-induced cAMP formation assays, supra, it is readily apparent that the VIP antagonists of the present invention are able to differentiate between the cAMP-associated VIP receptor(s) and the neuronal survival-linked VIP receptor(s). More particularly, it has been found that the NL-hybrid VIP antagonist has an affinity for both the cAMP-associated VIP receptor(s) and the neuronal survival-linked VIP receptors. In contrast, it has been found that the S-hybrid VIP antagonist and the S-NL-hybrid VIP antagonist have a higher affinity for the VIP receptor which is linked to the neuronal survival promoting-activity of VIP. Due to their ability to differentiate and discriminate between the various VIP receptors, the VIP antagonists of the present invention can be used in in vivo studies to delineate the physiological functions of VIP in the CNS and its behavioral consequences.

In yet a further aspect, the present invention provides a method of inhibiting circadian rhythm in a mammal, the method comprising administering to the mammal a vasoactive intestinal polypeptide (VIP) antagonist in an amount sufficient to effect inhibition, the antagonist comprising the following composition (SEQ ID NO.:1):

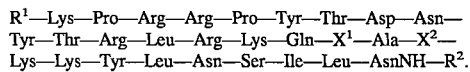

The previous discussion pertaining to $R^1$, $R^2$, $X^1$ and $X^2$ is fully applicable to the VIP antagonists used in this method of the present invention and, thus, it will not be repeated again with respect to this particular method. It should be noted, however, that within the scope of the above method, certain vasoactive intestinal polypeptide antagonists are preferred, namely those in which $R^1$ is H; $R^2$ is H; $X^1$ is a norleucine residue; $X^2$ is a valine residue. Equally preferred are VIP antagonists in which $R^1$ is $CH_3(CH_2)_{16}CO-$; $R^2$ is H; $X^1$ is a methionine residue; and $X^2$ is a valine residue.

It has been determined that a major site of VIP synthesis is the suprachiasmatic nucleus of the hypothalamus, the brain area controlling biological rhythms (Card, et al., *Cell and Tissue Res.*, 252:307 (1988)). Moreover, it has been determined that VIP mRNA oscillates during the day/night cycle, with peak levels of VIP mRNA being present at nighttime (Gozes, et al., *Neurosci. Res. Comms.*, 5:83 (1989); Albers, et al., *Mol. Brain Res.*, 7:85 (1990)). Using the receptor-discriminating VIP antagonists of the present invention, it has now been discovered that VIP-stimulated cAMP formation is required for the maintenance of the biological clock.

Figure 4A:
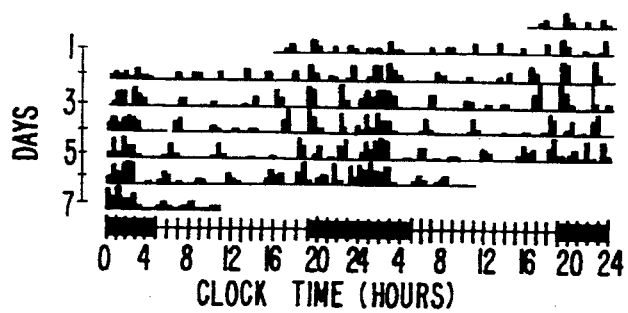
FIGS. 4(A–J). VIP antagonism disturbed the biological clock via a cAMP-mediated mechanism. Newborn rat pups (Sprague-Dawley, locally bread, Yoxheam, Israel) were chronically injected with VIP analogues (5 μg of each analogue/50 μl/day, subcutaneous), for 28 consecutive days. The vehicle of injection was either 0.01M acetic acid or 15% dimethylsulfoxide (for the lipophilic peptides). On day 21, the animals were placed each one in a separate cage and their locomotive activity was continuously measured. The pattern of locomotive activity was measured using an animal monitoring system with an infrared detector for 7 days (A, C, E, G, I). The spectral periods of rhythm in the activity data was detected by a special statistical method because of the short computer sampling period. This method uses probability (P) of fitting sine waves with different periods (from 3–40 hours) and using 1/P in a log scale to emphasize the significant period of rhythms (B, D, F, H, J, and see, Ticher, A., and I.E. Ashkenazi, submitted for publication; Mattes, et al., *Chronobiology Int'l*, 8:460 (1991)). A, B, control animals; C, D, NL-hybrid treatment; E, F, NL-hybrid+NL-VIP treatment, G, H, NL-VIP; I, J, S-NL-hybrid treatment. At least four animals were included in each treatment group.
Figure 4B:
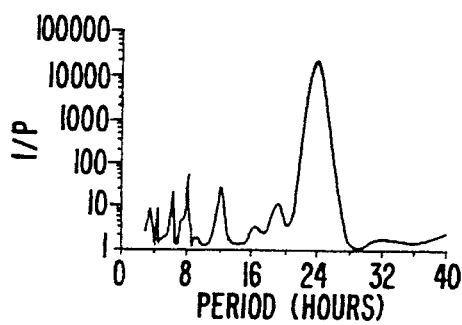
Figure 4C:
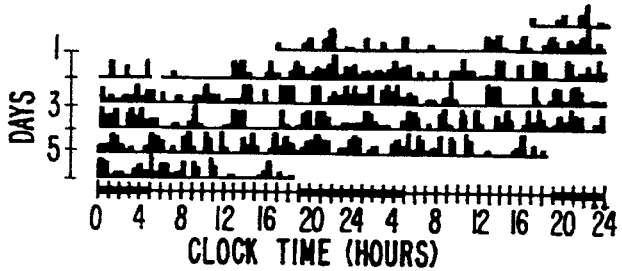
Figure 4D:
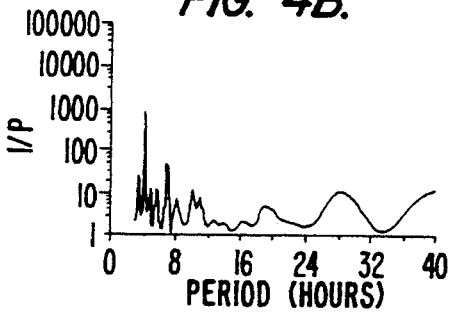
Figure 4E:
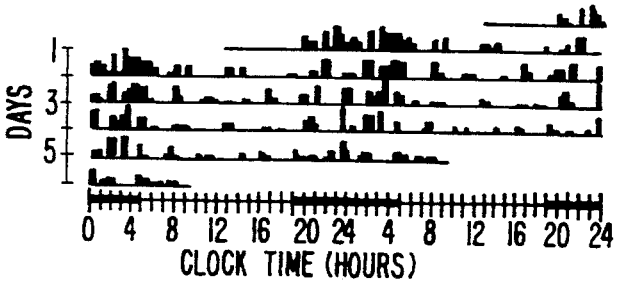
Figure 4F:
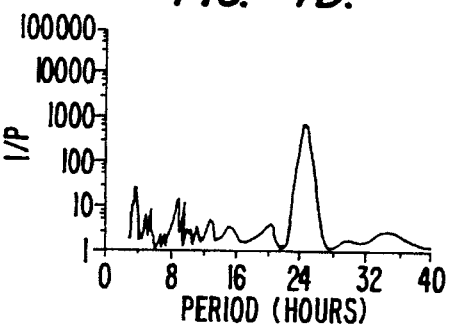
Figure 4G:
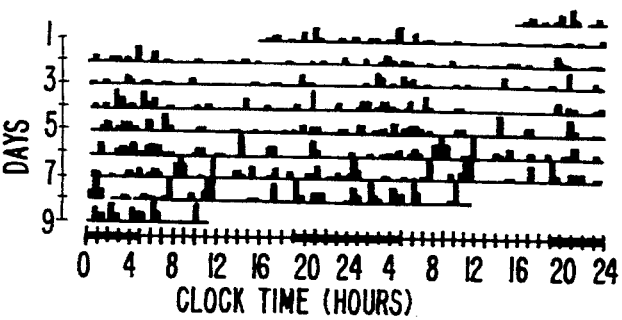
Figure 4H:
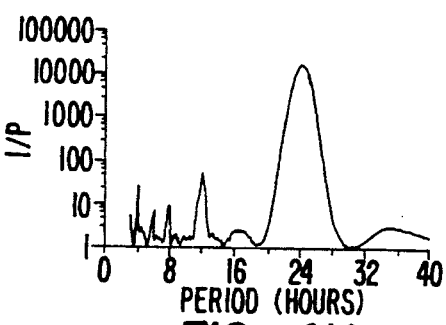
Figure 4I:
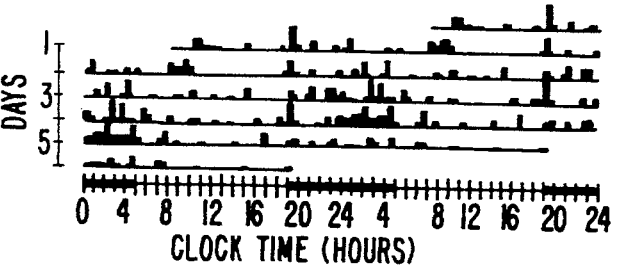
Figure 4J:
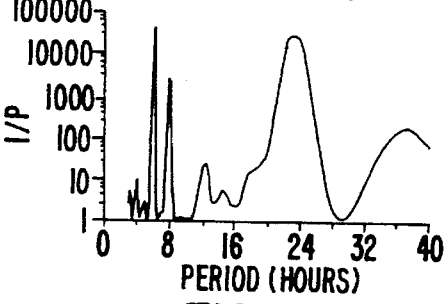

The question as to whether or not VIP is directly involved with the determination of the biological clock was investigated by specifically inhibiting VIP function utilizing chronic daily injection (subcutaneous) of the various VIP antagonists. FIG. 4 shows spectral analysis of activity rhythms presented by the probability of fitting different cosine curves to the activity data. While control animals showed 24 hours periodicity (FIG. 4A, activity data; FIG. 4B, spectral analysis), injection of the NL-hybrid VIP antagonist of the present invention abolished this 24 hours periodicity, with an overall increase in the activity of the animals (FIGS. 4C and 4D). This was reversed by co-administration of the NL-hybrid VIP antagonist and NL-VIP (FIGS. 4E and 4F); NL-VIP by itself had no significant effect (FIGS. 4G and 4H). In contrast, it was found that injection of the S-NL-hybrid VIP antagonist had no effect on the 24 hours periodicity, although, some changes in the diurnal rhythms occurred and the animals exhibited some sporadic activities with divergent. periodicity (FIGS. 4I and 4J). Similar results were obtained after cannulation and direct administration of the VIP analogues to the SCN (data not shown).

The results set forth above clearly demonstrate an involvement of VIP-stimulated cAMP formation in the determination of the biological clock. Indeed, the results obtained using the VIP antagonists of the present invention indicate an involvement of VIP-stimulated cAMP in the determination of rhythmicity in vivo. These findings are consisted with prior findings which showed that cAMP is able to reset the mammalian circadian clock in the SCN in vitro (Prosser, et al., *J. Neurosci.*, 9:1073 (1989); Prosser and Gillette, *Brain Res.*, 568:185 (1991)). As such, it is readily apparent that by administering to a mammal an effective amount of the VIP antagonist of the present invention (e.g., the NL-hybrid VIP antagonist), one can effectively inhibit, i.e., antagonize, circadian rhythm in the mammal.

In yet another aspect, the present invention provides a method of inhibiting VIP-induced neuroblastoma cell division, the method comprising contacting the neuroblastoma cells with a vasoactive intestinal polypeptide (VIP) antagonist in an amount sufficient to effect the inhibition, the antagonist comprising the following amino acid sequence (SEQ ID NO.:1):

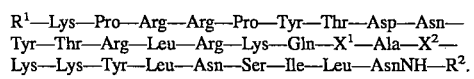

The previous discussion pertaining to $R^1$, $R^2$, $X^1$ and $X^2$ is fully applicable to the VIP antagonists used in this method of the present invention and, thus, it will not be repeated herein again with respect to this particular method. It should be noted, however, that within the scope of the above method, certain vasoactive intestinal polypeptide antagonists are preferred, namely those in which $R^1$ is H; $R^2$ is H; $X^1$ is a norleucine residue; $X^2$ is a valine residue. Equally preferred are VIP antagonists in which $R^1$ is H; $R^2$ is H; $X^1$ is a methionine residue; and $X^2$ is a valine residue. Also equally preferred are VIP antagonists in which $R^1$ is $CH_3(CH_2)_{16}CO-$; $R^2$ is H; $X^1$ is a methionine residue; and $X^2$ is a valine residue.

Neuroblastoma, a tumor of the sympathetic nervous system, is the most common solid malignancy of children less than 5 years of age. Previous studies have suggested that VIP may be an autocrine growth factor in neuroblastoma, based on the observations that VIP induces cell differentiation of neuroblastoma cell lines (O'Dorisio, et al., *Regulatory Peptides*, 37:213–226 (1992). In addition, in human neuroblastoma cell line (NMB), VIP is now shown to have mitogenic activity.

To assay for cell differentiation of neuroblastoma cell lines, namely the effects of the VIP antagonists on neuroblastoma cell division, a number of different assays can be used including, for example, direct cell counting, thymidine incorporation, determination of cells incorporating the nucleotide BRDU, as an index of mitotic cells, and, in cancer cells, the ability to form colonies in soft agar and the ability to propagate in nude mice. All of the above assays have been recently used in a number of studies (see, e.g., Moody, et al., *Proc. Natl. Acad. Sci, USA*, 90:4345 (1993); Wollman, et al., *Brain Res.*, 624:339 (1993); and Gressens, et al., *Nature*, 362:155 (1993).

Human neuroblastoma (NMB) cells were originally obtained during a bone marrow biopsy of a 10 months old girl (Brodeur, et al., *Cancer*, 40:2256–2263 (1977)). Previous examinations of this cell line revealed a near tetraploid karyotype and an amplification of the N-myc oncogene (Schwab, et al., *Nature*, 305:245–248(1983)). A potential role was offered for VIP as an inhibitor of neuroblastoma (cell line IMR 32) growth and, thus, the generality of this effect was investigated. The results of this investigation show that a 24 hour treatment with VIP stimulated neuroblastoma (NMB) cell division, in a dose-dependent manner, as measured 48 hours after plating by cell counts and thymidine incorporation (See, FIGS. 5 and 6, $EC_{50}=5\times10^{-7}M$). Interestingly, there was a peak of activity at 1 µM concentration, which decreased thereafter. This decrease could perhaps be explained by receptor desensitization (Rosselin, et al., in: *Vasoactive Intestinal Peptide and Related Peptides* (Said and Mutt (eds.), *Annals of the N.Y. Acad. Sci.*, 527:220–237 (1988)), a phenomenon which has previously been observed in other VIP-related activities, e.g., promotion of neuronal survival (Brenneman, et al., supra, 1990; Gozes, et al., *J. Pharmacol. and Exp. Therap.*, 257:959–966 (1991)).

Further, it has been found that VIP bound specifically to receptors on these neuroblastoma cells and the receptor expression was developmentally determined, exhibiting an about 10-fold higher affinity in younger cells (24 hrs. after plating, $K_d$ of 0.2 µM) as compared to older cells (48 hrs. after plating, $K_d$ of 2 µM, FIG. 7). The $K_d$ of 0.2 µM corresponds closely to the $EC_{50}=5\times10^{-7}M$, for VIP-stimulated cell multiplication (VIP was added 24 hours after plating and incubated for additional 24 hours, FIGS. 5 and 6). Moreover, a four-fold decrease was observed in the $B_{max}$ of 48 hours old cultures ($B_{max}=1.5\times10^{-14}$ moles/mg) as compared to 24 hours old cultures ($B_{max}=6\times10^{-14}$ moles/mg; FIG. 7). Indeed, when VIP was added 48 hours after plating (i.e., when the reduced number of receptors available were at their low affinity state (FIG. 7)) for an additional 24 hours incubation, it did not stimulate mitosis. Moreover, Northern blot hybridizations indicated the existence of VIP mRNA in these neuroblastoma cells. In FIG. 8, a 2100 bases band representing VIP mRNA (and traces of a high molecular weight hybridizing band, which probably represents a VIP mRNA precursor (Gozes, et al., *Mol. Brain Res.* 2:137–148 (1987); Gozes, et al., *Neuroendocrinology*, 47:27–31 (1988)) can be identified. Taken together, the data suggests that VIP acts as an autocrine regulator of neuroblastoma proliferation.

In addition, it has now been discovered that the VIP antagonists of the present invention can be used to inhibit neuroblastoma growth (i.e., cell division). More particularly, it has been found that the hybrid VIP antagonist potently blocks thymidine incorporation in neuroblastoma cells in a dose dependent manner (See, FIGS. 9 and 10), the effects of which are more robust in younger neuroblastoma cells, when the affinity of the VIP to the receptor is higher. As such, by contacting neuroblastoma cells with a VIP antagonist (e.g., the hybrid VIP antagonist or the NL-hybrid VIP antagonist), one can effectively inhibit the growth, i.e., cell division, of neuroblastoma cells.

In still yet another aspect, the present invention provides pharmaceutical compositions comprising one of the previously described VIP antagonists in an amount sufficient to inhibit VIP associated activity, and a pharmaceutically acceptable diluent, carrier or excipient. The pharmaceutical compositions of the present invention are suitable for use in a variety of drug delivery systems. Suitable formulations for use in the present invention are found in *Remington's Pharmaceutical Sciences* (Mack Publishing Company, Philadelphia, Pa., 17th ed. (1985)), which is incorporated herein by reference. In addition, for a brief review of methods for drug delivery, see, Langer, *Science* 249:1527–1533 (1990), which is incorporated herein by reference.

As described above, VIP is associated with the etiology of neuroblastoma and a number of different cancers (e.g., NSCLC), suggesting that VIP is associated with tumorigenesis. Moreover, as described above, the VIP antagonists of the present invention have been shown to inhibit VIP-induced neuroblastoma cell division and to inhibit the growth of VIP receptor containing tumor cells. As such, the present invention provides for therapeutic compositions or medicaments comprising one of the VIP antagonists described hereinabove in combination with a pharmaceutically acceptable excipient, wherein the amount of the VIP antagonist is sufficient to provide a therapeutic effect.

In a therapeutic application, the VIP antagonists of the present invention are embodied in pharmaceutical compositions intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration which comprise a solution of a VIP antagonist, as described above, dissolved or suspended in an acceptable carrier, preferably an aqueous carrier. A variety of aqueous carriers may be used including, for example, water, buffered water, 0.4% saline, 0.3% glycine, hyaluronic acid and the like. These compositions may be sterilized by conventional, well known sterilization techniques or, they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient and more preferably at a concentration of 25%–75%.

For aerosol administration, the polypeptides are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

In therapeutic applications, the VIP antagonists of the invention are administered to a patient in an amount sufficient to antagonize (i.e., inhibit) VIP-associated activity. An amount adequate to accomplish this is defined as "therapeutically effective dose." Amounts effective for this use will depend on, for example, the particular VIP antagonist employed, the VIP-associated activity to be inhibited or antagonized, the manner of administration, the weight and general state of health of the patient, and the judgment of the prescribing physician. For example, for inhibition of tumor growth (e.g., NSLC or neuroblastoma), an amount of VIP antagonist falling within the range of 0.35 μg to 3.5 μg per 100 g tumor, injected directly into the solid tumor would be a therapeutically effective amount. For inhibition of circadian rhythm, an amount of VIP antagonist falling within the range of a 1 to 10 mg dose given intranasally once a day (in the evening) would be a therapeutically effective amount.

The invention will be described in greater detail by way of specific examples. The following examples are ofrbred for illustrative purposes, and are intended neither to limit or define the invention in any manner.

EXAMPLES: GENERAL PROCEDURES

A. Synthesis of the VIP Antagonists

The peptides, i.e., VIP antagonists, of the present invention were synthesized using the solid-phase strategy, as described by Barany and Merrifield, *Solid-Phase Peptide Synthesis in The Peptides: Analysis, Synthesis, Biology* (Gross and Meienhofer (eds.) Academic press, New York, vol. 2, pp. 3–284 (1980)), employing manual as well as automatic (ABIMED AMS 422 Peptide Synthesizer) procedures.

1. Peptide Synthesis—Manual Procedure

The corresponding peptide chain was assembled manually in a mechanical shaker according to the general principles of the solid-phase methodology of Barany and Merrifield, supra, on a 4-(α-[2,4-dimethoxyphenyl]Fmoc-aminomethyl)phenoxy resin, purchased from Nova, Switzerland. The following solvents were analytical products purchased from Merck, Germany: methylene chloride ($CH_2Cl_2$), N-methylpyrrolidone (NMP) and dimethyl formamide (DMF). Trifluoroacetic acid (TFA), diisopropylethylamine (DIEA) and N,N'-dicyclohexylcarbodiimide (DCC) were purchased from Aldrich, U.S.A. 1-Hydroxybenzotriazole (HOBt) was obtained from Nova, Switzerland. All protected amino acid derivatives (Fmoc-AA) were of the L-configuration and were obtained from Bachem, Switzerland. Nα-amino acid functions were protected throughout the synthesis by the fluorenylmethoxycarbonyl (Fmoc) group. Side chain functions were protected as follows: serine (Ser), aspartic acid (Asp) and threonine (Thr) with t-butyl; lysine (Lys) with t-butyloxycarbonyl; and arginine (Arg) with methoxytrimethylphenylsulfonyl (Mtr); glummine and asparagine with trityl (Trt).

The synthesis was initiated by removal of the Fmoc-group, from the commercial polymer: 4-(α-[2,4-dimethoxyphenyl]-Fmoc-aminomethyl)phenoxy resin (0.47 mmol of amino group/g), according to steps 1 and 2 of Table IV, infra (see, the protocol outlined in Table IV). 10 g of polymer, contained in 2 reaction vessels, were employed. The volume of solvents used was 20–25 mL in each vessel. Assembly of the peptide chain was initiated by coupling Fmoc-Asn (0.92 g, 4 mmol) to the resin (5 g) using DCC (0.84 g, 4 mmol) and HOBt (0.55 g, 4 mmol) as agents. The coupling was repeated. Loading (0.39 mmol/g) was determined by amino acid analysis. Unreacted residual amino groups on the polymer were capped by reacting with acetic anhydride (10%) and diisopropylethylamine (5%) in $CH_2Cl_2$. The peptide chain assembly was started from the Fmoc-Asn-resin, following the protocol outlined in Table IV.

TABLE IV

Protocol Used to Prepare the VIP Antagonists

| Step | Reagents | min. |
|---|---|---|
| 1 | 10% piperidine/DMF | 5 |
| 2 | 20% piperidine/DMF | 15 |
| 3 | DMF | 2 |
| 4 | DMF | 2 |
| 5 | DMF | 2 |
| 6 | $CH_2Cl_2$ | 2 |
| 7 | $CH_2Cl_2$ | 2 |
| 8 | NMP | 2 |
| 9 | Ninhydrin test | |
| 10 | Fmoc-amino acid/HOBt/DCC (molar ratio 1:1:1 in NMP preactivation) | |
| 11 | DMF | 2 × 2 |
| 12 | $CH_2Cl_2$ | 2 |
| 13 | $CH_2Cl_2$ | 2 |
| 14 | $CH_2Cl_2$ | 2 |
| 15 | Ninhydrin test | |
| 16 | 10% $Ac_2O$ + 5% DIEA in $CH_2Cl_2$ | 3 |
| 17 | 10% $Ac_2O$ in $CHCl_2$ | 5 |
| 18 | $CH_2Cl_2$ | 2 |
| 19 | $CH_2Cl_2$ | 2 |
| 20 | $CH_2Cl_2$ | 2 |
| 21 | DMF | 2 |

Solvents for all washings and reactions were measured to volumes of 10 mL/g resin, except for coupling (i.e., step 10) when volumes of about 5 mL/g resin were employed. All couplings were performed using HOBt active esters of Fmoc-amino acid derivatives, prepared by DCC prior to each coupling step. A molar ratio of 2:1 of Fmoc-amino acid 1-hydroxybenzotriazole ester (i.e., Fmoc-AA-OBt) and α-amino group of growing peptide chain, respectively, was employed for couplings. Coupling reactions were monitored by boiling a few mg (i.e., about 3 mg) of polymer in a solution of ninhydrin in pyridine-water for 2 min. Coupling of Fmoc-amino acids was repeated two or more times to ensure complete reaction. In the second and, when necessary, other additional couplings, half of the amount of Fmoc-AA-OBt was used. Proceeding steps, aimed at addition of the next amino acid were initiated only after a negative ninhydrin test (See, step 15 of the protocol in Table IV). As a rule, after completion of each coupling step, residual amine groups were capped by treating the resin with acetic anhydride (10%) and diisopropylethylamine (5%) in methylene chloride.

Following completion of the peptide chain assembly, the N-terminal Fmoc-protecting group was removed, as usual, by piperidine in DMF. For preparation of stearyl-VIP antagonists, the newly free α-amino group was further coupled (in each reaction vessel) to stearic acid (0.74 g, 4 mmol) using DCC (0.84 g, 1 mmol) and HOBt (0.54 g, 4 mmol) as reagents. The reaction proceeded for 120 min and was repeated twice. The resin containing the fully assembled peptide-chain was washed with $CH_2Cl_2$ according to protocol, and then dried over $P_2O_5$ under vacuum overnight. Deblocking of protecting groups and cleavage of the peptide (with or without the terminal stearyl group) from the resin was achieved as follows: 1 g of dried resin was placed in a 100 cc flask to which thioanisole (2 mL) and ethanedithiol (2 mL) were added. The mixture was cooled to 4° C. in an ice bath and 20 mL of trifluoroacetic acid were added, and 5 min later trifluoromethanesulfonic acid (2 mL) was also added. The mixture was gently stirred at room temperature for 23 hr.

The reaction mixture was then cooled to 4° C. and poured into 500 mL of dry ether. After stirring for 60 min at 4° C., the solid material (resin and peptide) was filtered on a scinter funnel, washed with dry ether, dried and then extracted with 50% aqueous acetic acid (100 mL). The solution obtained, containing the peptide, was concentrated in high vacuum and the residue (about 15 mL) was directly loaded on a Sephadex G25 column (45×6 cm). The column was eluted with 0.1N acetic acid at a flow rate of 45 mL/1 hr. Elution was monitored at 274 nm. Lyophilization of the aqueous solution, containing the desired fraction, yielded the peptide free of the aromatic additives added as scavengers at the acidolytic cleavage step. Yield was about 400 mg of a white powder.

The material showed the required amino acid content and ratio as revealed by amino acid analysis following exhaustive acid hydrolysis.

Further purification by high perlbrmance liquid chromatography (HPLC) was carried out on the Sephadex-fractionatecl products. HPLC purification can, however, be performed on the crude peptides. Purifications were achieved on Merck RP-8 column (7 µM, 250×25 mm column). The peptides were applied in 35% acetonitrile in water and eluted with a linear gradient established between 35% acetonitrile and 0.1% TFA in water and 0.1% TFA in 75% acetonitrile in water at a flow rate of 10 mL/min. Fractions were collected and cuts made after inspection by analytical HPLC. Derived fractions were pooled and lyophilized. Yield of the pure peptides was 30-35%.

2. Peptide Synthesis—Automatic Procedure

Synthesis of the VIP antagonists, with or without stearyl terminal groups, was also achieved by automatic procedure employing an ABIMED AMS 422 synthesizer (ABIMED (Langenfeld, Germany)) using the commercially available protocols via the Fmoc-strategy. All protected amino acid derivatives were as previously outlined for the manual procedure with one exception, i.e., Fmoc-Arg (Pmc) (PMC= 2,2,5,7,8-pentamethylchroman-6-sulphonyl) replaced Fmoc-Arg (Mtr). PyBOP, i.e., benzotriazolyl-N-oxy-tris-(dimethylamino)phosphonium hexafluorophosphate, was used as a coupling agent. Peptide chains were assembled, as above, on a 4-([2',4'-dimethoxyphenyl]-Fmoc-aminoethyl)-phenoxy resin (Rink Amide Resin (Nova, Switzerland)). Final cleavage of peptide chain from the resin along with side chain deprotection was achieved as follows:

3. Cleavage of Peptides Synthesized with the AMS 422

| Cleavage mixture: | |
|---|---|
| 90% | TFA (trifluoroacetic acid) |
| 5% | water |
| 5% | Triethylsilane |

The resin, 100 mg, loaded with peptide was incubated for 30 min with 3 mL cleavage mixture inside the reaction column used for solid phase synthesis. After 30 min, the reaction mixture is separated from the cleaved resin, and the cleavage is continued for an additional 90 min. The cleaved peptide is precipitated with ice cold ether (i.e., tert-butylmethyl-ether) and centrifugated (4° C., 2000 rpm). The solution was decanted and the pellet was mixed again with ether and centrifugated. This step was repeat a second time. The pellet was dissolved in water and frozen for lyophilization. Purification of crude peptides was performed as described above.

4. Synthesis of VIP Antagonists Having $R^1=C_1$ to $C_{20}$ Alkyl

The peptide chain of the VIP antagonists is assembled on the polymeric support, i.e., p-methylbenzhydrylamine (MBHA) resin, (containing 0.39 mmol Asn/1 g) as described in (1) above. After incorporation of the last amino acid residue (i.e., histidine), the N-α-protecting group (t-Boc) is removed by TFA, the polymer is treated with diisopropylethylamine (DIEA), washed and ninhydrin tested. The polymer is then suspended in ethyl alcohol (1 g/10 mL), the corresponding aldehyde R'—CH=O (R'=hydrophobic moiety of any other aidehyde) is added (3–4 equivalents of aldehyde to 1 equivalent of free N-terminal amino group), and the mixture is gently agitated overnight at room temperature. The polymer is filtered, washed with ethanol (3×10 mL), resuspended in ethanol and $NaBH_4$ (3–4 equivalents of reducing agent to 1 equivalent of Schiff base; R'—CH=N— —), and the mixture is gently agitated for 2 hr at room temperature. Alternatively, $NaBH_3CN$ (3–4 equivalents to 1 equivalent of Schiff base) can be employed (in the presence of 0.1–0.2 mL, of acetic acid). Condensation and reduction reactions can also be performed in other organic solvents, such as DMF or NMP. Following completion of the reduction reaction, the polymer is filtered, washed and dried, and treated with the cleavage mixture as described above. The crude product is purified in the same manner as described above to afford the desired final products.

Purity of the product was ascertained by analytical HPLC (Merck RP-8, 125×4 mm column) and amino acid analysis, following exhaustive acid hydrolysis (6N HCl), gave the expected values of each constituent amino acid.

Molecular weights of the various synthetic peptides were ascertained by mass spectrometry (VG Tofspec, Laser Desorphon Mass Spectrometer, Fison Instruments, England).

B. Cell culture and immunocytochemistry

Rat cortical astrocytes were prepared by previously described methods (McCarthy and Partlow, *Brain Res.*, 114: 391–414 (1976); Evans, et al., *J. Neurochem.*, 43:131–138 (1984)). Binding studies were conducted 3 to 5 days after replating. Astrocyte cultures were maintained at all times in 10% fetal. calf serum in Eagle's MEM. The cell composition of these cultures was determined by NSE and GFAP immunocytochemistry (Brenneman, et al., *J. Cell Biol.*, 104:1603–1610 (1987)). These analyses indicated that the cultures contained no detectable NSE-positive cells and that more than 95% of the cells stained with antisera to GFAP. For assays of neuronal cell functions, several preparations of CNS derived tissue were utilized. To investigate the effects of the various hybrid antagonists on neuronal survival, dissociated mouse spinal cord cultures (obtained from 12-day-old embryos) were used using previously described methods (Brenneman et al., *Dev. Brain Res.*, 9:13–27 (1983)). Briefly, cells were plated in 10% horse serum and 10% fetal calf serum in MEM. One day after plating, the medium was changed to 5% horse serum supplemented with defined medium components (Brenneman, et al., supra, (1987)). After nine days in vitro, the cultures were given a complete change of medium and treated with the VIP antagonists. The duration of treatment was from day 9 to day 14, after which the cultures were fixed for immunocytochemistry for NSE (i.e., neuron specific enolase, a well-defined neuronal marker). Cell counts were performed on 100 fields, with a total area of 60 mm. Neurons were counted without knowledge of treatment. Similar cell preparations were also used for binding studies.

NSCLC cells were propagated as described by Moody, et al., *Proc. Natl. Acad. Sci. U.S.A.*, 90:4345 (1993); and neuroblastoma cells were propagated as described by Wollman, et al., *Brain. Res.*, 624:339 (1993).

C. Radioligand Binding Studies

VIP binding studies were conducted on intact cells at 4° C., using phosphate-buffered saline containing 0.1% bovine serum albumin. Previous work indicated that a short-term exposure to VIP resulted in an internalization of the peptide receptors complex into clear endosomal vesicles, with a half-time in minutes (Boissard, et al., *Cancer Res.*, 46:4406–4413 (1986)). VIP is degraded in lysosomes or may serve as an intracellular effector. Most VIP receptors are recycled to the cell surface (Luis, et al., *Biochemie*, 70:1311–1322 (1988)). The internationalization is tissue specific (Antaunis, et al., *Am. J. Physiol.*, 256:G689–G697 (1989)) and is blocked at 4° C. (Svoboda, et al., *Eur. J. Biochem.*, 176:707–713 (1988)). Therefore, all binding studies were conducted at 4° C. on intact cells from the various CNS preparations described above. Time course experiments conducted in the astrocyte cultures indicated that equilibrium binding was achieved during 1 hr of incubation with 50 pM $^{125}$I-labeled VIP in the cell cultures (0.3–0.5 mg of protein per 35-mm tissue culture dish). Specific VIP binding did not increase between 1 and 3 hr of incubation; however, nonspecific binding increased throughout the 3-hr incubation. The labeled ligand was [$^{125}$I]-VIP at the tyr$^{22}$ (2000 Ci/mmol, Amersham Corp., Arlington Heights, Ill.) or iodinated VIP labeled at tyr$^{10}$ as well as tyr$^{22}$, with a similar specific activity, purchased from New England Nuclear (Boston, Mass.) the same results were obtained with both. Additionally, VIP was labeled by us using the chloramine T method. Briefly, 100 µg of peptide were incubated with [$^{125}$I]-Na (1 mCi, Amersham, Inc.) in the presence of chloramine T (15 µg, Sigma Chemical Corp.). After three minutes, the reaction was quenched by the addition of sodium metabisulfite (35 µg). After three additional minutes, 10 µL of 1% KI were added and free labeled iodine was separated from the radioactive peptide by Sephadex G-25 gel filtration. Elution was conducted in phosphate buffered saline (PBS) in the presence of 1% bovine serum albumin. Iodinated peptides were analyzed for purity and molecular identity by reverse phase HPLC utilizing a silica C-8 column (RP-8, 7 µm, 250×10 mm).

Cultures were preincubated with either VIP on the antagonist (1 pM-10 µM) for 30 min before the addition of 50 pM [$^{125}$I]-VIP. The 0.5-hr preincubation with the competing nonlabeled peptide was done to minimize nonspecific binding of the radioactive peptide. Labeled ligand was then incubated with the cultures of the radioactive peptide. Labeled ligand was then incubated with the cultures for 1 hr; the media was thereafter removed and cells were washed 3 times by the addition and rapid removal of 1 mL of phosphate-buffered saline (at 4° C.). The labeled cells were then dissolved in 0.2N NaOH and transferred for radioactivity counting. The binding parameters of the displacement curves were determined by the ACCUFIT program (London Software, Chagrin Falls, Ohio). This program implements previously described methods of analysis of nonlinear least-square regression (Feldman, *Anal. Biochem.*, 48:317–338 (1972); Linden, *J. Cyclic Nucleotide Res.*, 8:163–172 (1982); and Unnerstall, "Computer-associated analysis of binding data," in *Methods in Neurotransmitter Receptor Analysis* (Yamamura, Enna and Kuher (eds.), Raven Press, New York (1990)). The $K_d$, $K_i$ and $K_B$ values were computed assuming equilibrium conditions.

D. c-fos mRNA Assays

For the c-fos experiments, SCLC cells were cultured with SIT medium containing 0.5% fetal bovine serum. After 4 hours, the cells were treated with stimuli such as 10 nM BN for 60 min. Total RNA was isolated using the guanidinium isothiocyanate (GIT) method. Ten µg of denatured RNA was separated in a 0.66M formaldehyde 1% agarose gel as previously described. The gel was treated with ethidium bromide tp assess RNA integrity. The RNA was blotted onto a nitrocellulose membrane overnight and the membrane hybridized with a c-fos probe labelled with $^{32}$P-dCTP using a Bethesda Research Laboratories random priming kit. The membrane was exposed to Kodax XAR-2 film at 80° C. for 1 day and the autoradiogram developed. The autoradiogram were analyzed using a Molecular Dynamics densitometer.

E. cAMP Assays

Rat astrocytes were maintained in cell culture as described above. The accumulation of cAMP was measured by radio-immunoassay (NEN kit, New England Nuclear) from cold trichloro acetic acid extracts (Evans et al., supra, 1984). The various VIP antagonists were preincubated with the astrocyte cultures for 5 min before the incubation with 1 µM VIP, for 10 additional min. The affinity of the VIP antagonists for the adenylate cyclase-coupled VIP receptor and for the VIP receptor linked to neuronal survival (see above) were assessed by measuring the ability of the VIP antagonists to cause a parallel rightward shift of the VIP dose-response curve (Mayer, *J. Pharmacol. Exp. Ther.*, 161:116–125 ((1972)). The dissociation constants for the VIP antagonists were calculated from the equation $K_a$= [antagonist]/(CR–1), where CR=the ratio of equiactive concentrations of VIP in the presence and absence of the given concentration of antagonist. Equiactive concentrations (EC) of VIP were assessed at the midpoints of the stimulation curves.

F. Thymidine Incorporation

For thymidine incorporation, cells were exposed to $^3$H-thymidine (4 µCi/dish) for a 24 hour incubation period. Medium was then removed and 0.2N NaOH was added to the 35 mm tissue culture dishes (0.5 mL/dish) and incubated for about 20 minutes. The cell suspension was filtered through GF/C filter paper pre-soaked with 0.3% polyethylenimine. Filters were washed with 25 mL H$_2$O and 5 mL ethanol, dried and counted for radioactivity.

G. Circadian Motor Activity Rhythms

Animals were each placed in a separate cage and motor activity was continuously recorded for 6–9 days, using an animal monitoring system with an infrared detector. Spectral analysis of motor activity rhythms is then determined by the fitting of different cosine curves to the activity data (see, Mattes, et al., *Chronobiology Int'l*, 8:460 (1991)).

All publications mentioned hereinabove are hereby incorporated in their entirety by reference.

While the foregoing invention has been described above in some detail for purposes of clarity and understanding, it will be appreciated by one skilled in the art from a reading of this disclosure that various changes in form and detail can be made without departing from the spirit and scope of the invention.

What is claimed is:

1. A vasoactive intestinal polypeptide (VIP) antagonist, said antagonist consisting of the following amino acid sequence:

$R^1$—Lys—Pro—Arg—Arg—Pro—Tyr—Thr—Asp—Asn—Tyr—Thr—Arg—Leu—Arg—Lys—Gln—$X^1$—Ala—$X^2$—Lys—Lys—Tyr—Leu—Asn—Ser—Ile—Leu—AsnNH—$R^2$ in which:

$R^1$ and $R^2$ are members independently selected from the group consisting of hydrogen, $C_1$ to $C_{20}$ alkyl and $C_1$ to $C_{20}$ acyl, provided that at least one of $R^1$ or $R^2$ is hydrogen; and $X^1$ and $X^2$ are members independently selected from the group consisting of naturally occurring amino acids and amino acid mimetics of hydrophobic character;

and conservative modifications thereof, with the proviso that said antagonist is not the following compound:

Lys-Pro-Arg-Arg-Pro-Tyr-Thr-Asp-Asn-Tyr-Thr-Arg-Leu-Arg-Lys-Gln-Met-Ala-Val-Lys-Lys-Tyr-Leu-Asn-Ser-Ile-Leu-Asn.

2. A vasoactive intestinal polypeptide (VIP) antagonist in accordance with claim 1 wherein:

$X^1$ and $X^2$ are members independently selected from the group consisting of naturally occurring amino acids and amino acid mimetics of hydrophobic character.

3. A vasoactive intestinal polypeptide (VIP) antagonist in accordance with claim 1 wherein:

$R^1$ is H;
  $R^2$ is H;
  $X^1$ is a norleucine residue; and
  $X^2$ is a valine residue.

4. A vasoactive intestinal polypeptide (VIP) antagonist in accordance with claim 1 wherein:
$R^1$ is $CH_3(CH_2)_{16}CO—$;
$R^2$ is H;
$X^1$ is a norleucine residue; and
$X^2$ is a valine residue.

5. A vasoactive intestinal polypeptide (VIP) antagonist in accordance with claim 1 wherein:
$R^1$ is $CH_3(CH_2)_{16}CO—$;
$R^2$ is H;
$X^1$ is a methionine residue; and
$X^2$ is a valine residue.

6. A method of antagonizing VIP-associated activity in a mammal, said method comprising administering to said mammal a vasoactive intestinal polypeptide (VIP) antagonist in an amount sufficient to effect said antagonism, said antagonist consisting of the following amino acid sequence;

$R^1$—Lys—Pro—Arg—Arg—Pro—Tyr—Thr—Asp—Asn—Tyr—Thr—Arg—Leu—Arg—Lys—Gln—$X^1$—Ala—$X^2$—Lys—Lys—Tyr—Leu—Asn—Ser—Ile—Leu—AsnNH—$R^2$ in which:
$R^1$ and $R^2$ are members independently selected from the group consisting of hydrogen, $C_1$ to $C_{20}$ alkyl and $C_1$ to $C_{20}$ acyl, provided that at least one of $R^1$ or $R^2$ is hydrogen; and
$X^1$ and $X^2$ are members independently selected from the group consisting of naturally occuring amino acids and amino acid mimetics of hydrophobic character;
and conservation modifications thereof, with the proviso that said antagonisat is not the following compound Lys-Pro-Arg-Arg-Pro-Tyr-Thr-Asp-Asn-Tyr-Thr-Arg-Leu-Arg-Lys-Gln-Met-Ala-Val-Lys-Lys-Tyr-Leu-Asn-Ser-Ile-Leu-Asn.

7. A method in accordance with claim 6 wherein
$R^1$ of said antagonist is H;
$R^2$ of said antagonist is H;
$X^1$ of said antagonist is a norleucine residue; and
$X^2$ of said antagonist is a valine residue.

8. A method in accordance with claim 6 wherein
$R^1$ of said antagonist is $CH_3(CH_2)_{16}CO—$;
$R^2$ of said antagonist is H;
$X^1$ of said antagonist is a norleucine residue; and
$X^2$ of said antagonist is a valine residue.

9. A method in accordance with claim 6 wherein
$R^1$ of said antagonist is $CH_3(CH_2)_{16}CO—$;
$R^2$ of said antagonist is H;
$X^1$ of said antagonist is a methionine residue; and
$X^2$ of said antagonist is a valine residue.

10. A method of inhibiting the growth of VIP receptor containing tumor cells selected from the group consisting of lung tumor cells and breast tumor cells, said method comprising contacting said tumor cells in vitro with a vasoacative intestinal polypeptide (VIP) antagonist in an amount sufficient to effect said inhibition, said antagonist consisting of the following amino acid sequence;

$R^1$—Lys—Pro—Arg—Arg—Pro—Tyr—Thr—Asp—Asn—Tyr—Thr—Arg—Leu—Arg—Lys—Gln—$X^1$—Ala—$X^2$—Lys—Lys—Tyr—Leu—Asn—Ser—Ile—Leu—AsnNH—$R^2$ in which:
$R^1$ and $R^2$ are members independently selected from the group consisting of hydrogen, $C_1$ to $C_{20}$ alkyl and $C_1$ to $C_{20}$ acyl, provided that at least one of $R^1$ or $R^2$ is hydrogen; and
$X^1$ and $X^2$ are members independently selected from the group consisting of naturally occuring amino acids and amino acid mimetics of hydrophobic character;
and conservative modifications thereof, with the proviso that said antagonist is not the following compound:

Lys-Pro-Arg-Arg-Pro-Tyr-Thr-Asp-Asn-Tyr-Thr-Arg-Leu-Arg-Lys-Gln-Met-Ala-Val-Lys-Lys-Tyr-Leu-Asn-Ser-Ile-Leu-Asn.

11. A method in accordance with claim 10 wherein
$R^1$ of said antagonist is H;
$R^2$ of said antagonist is H;
$X^1$ of said antagonist is a norleucine residue; and
$X^2$ of said antagonist is a valine residue.

12. A method in accordance with claim 10 wherein
$R^1$ of said antagonist is $CH_3(CH_2)_{16}CO—$;
$R^2$ of said antagonist is H;
$X^1$ of said antagonist is a norleucine residue; and
$X^2$ of said antagonist is a valine residue.

13. A method in accordance with claim 10 wherein
$R^1$ of said antagonist is $CH_3(CH_2)_{16}CO—$;
$R^2$ of said antagonist is H;
$X^1$ of said antagonist is a methionine residue; and
$X^2$ of said antagonist is a valine residue.

14. A method in accordance with claim 10 wherein said cells are non-small cell lung cancer cells.

15. A method of inducing neuronal cell death in vitro, said method comprising contacting said neruonal cells with a vasoactive intestinal polypeptide (VIP) antagonist in an amount sufficient to effect the health of said neuronal cells, said antagonist consisting of the following amino acid sequence:

$R^1$—Lys—Pro—Arg—Arg—Pro—Tyr—Thr—Asp—Asn—Tyr—Thr—Arg—Leu—Arg—Lys—Gln—$X^1$—Ala—$X^2$—Lys—Lys—Tyr—Leu—Asn—Ser—Ile—Leu—AsnNH—$R^2$ in which:
$R^1$ and $R^2$ are members independently selected from the group consisting of hydrogen, $C_1$ to $C_{20}$ alkyl and $C_1$ to $C_{20}$ acyl, provided that at least one of $R^1$ or $R^2$ is hydrogen; and
$X^1$ and $X^2$ are members independently selected from the group consisting of naturally occuring amino acids and amino acid mimetics of hydrophobic character;
and conservative modifications thereof, with the proviso that said antagonist is not the following compound:

Lys-Pro-Arg-Arg-Pro-Tyr-Thr-Asp-Asn-Tyr-Thr-Arg-Leu-Arg-Lys-Gln-Met-Ala-Val-Lys-Lys-Tyr-Leu-Asn-Ser-Ile-Leu-Asn.

16. A method in accordance with claim 15 wherein
$R^1$ of said antagonist is H;
$R^2$ of said antagonist is H;
$X^1$ of said antagonist is a norleucine residue; and
$X^2$ of said antagonist is a valine residue.

17. A method in accordance with claim 15 wherein
$R^1$ of said antagonist is $CH_3(CH_2)_{16}CO—$;
$R^2$ of said antagonist is H;
$X^1$ of said antagonist is a norleucine residue; and
$X^2$ of said antagonist is a valine residue.

18. A method in accordance with claim 15 wherein
$R^1$ of said antagonist is $CH_3(CH_2)_{16}CO—$;

$R^2$ of said antagonist is H;
$X^1$ of said antagonist is a methionine residue; and
$X^2$ of said antagonist is a valine residue.

19. A method of inhibiting circadian rhythm in a mammal, said method comprising administering to said mammal a vasoactive intestinal polypeptide (VIP) antagonist in an amount sufficient to effect said inhibition, said antagonist consisting of the following of the following amino acid sequence:

$R^1$—Lys—Pro—Arg—Arg—Pro—Tyr—Thr—Asp—Asn—Tyr—Thr—Arg—Leu—Arg—Lys—Gln—$X^1$—Ala—$X^2$—Lys—Lys—Tyr—Leu—Asn—Ser—Ile—Leu—AsnNH—$R^2$ in which:
$R^1$ and $R^2$ are members independently selected from the group consisting of hydrogen, $C_1$ to $C_{20}$ alkyl and $C_1$ to $C_{20}$ acyl, provided that at least one of $R^1$ or $R^2$ is hydrogen; and
$X^1$ and $X^2$ are members independently selected from the group consisting of naturally occurring amino acids and amino acid mimetics of hydrophobic character;
and conservative modifications thereof.

20. A method in accordance with claim 19 wherein
$R^1$ of said antagonist is H;
$R^2$ of said antagonist is H;
$X^1$ of said antagonist is a methionine residue; and
$X^2$ of said antagonist is a valine residue.

21. A method in accordance with claim 19 wherein
$R^1$ of said antagonist is H;
$R^2$ of said antagonist is H;
$X^1$ of said antagonist is a norleucine residue; and
$X^2$ of said antagonist is a valine residue.

22. A method of inhibiting neuroblastoma cell division in vitro, said method comprising contacting said neuroblastoma cells with a vasoactive intestinal polypeptide (VIP) antagonist in an amount sufficient to effect said inhibition, said antagonist consisting of the following amino acid sequence:

$R^1$—Lys—Pro—Arg—Arg—Pro—Tyr—Thr—Asp—Asn—Tyr—Thr—Arg—Leu—Arg—Lys—Gln—$X^1$—Ala—$X^2$—Lys—Lys—Tyr—Leu—Asn—Ser—Ile—Leu—AsnNH—$R^2$ in which:
$R^1$ and $R^2$ are members independently selected from the group consisting of hydrogen, $C_1$ to $C_{20}$ alkyl and $C_1$ to $C_{20}$ acyl, provided that at least one of $R^1$ or $R^2$ is hydrogen; and
$X^1$ and $X^2$ are members independently selected from the group consisting of naturally occurring amino acids and amino acid mimetics of hydrophobic character;
and conservative modifications thereof.

23. A method in accordance with claim 22 wherein
$R^1$ of said antagonist is H;
$R^2$ of said antagonist is H;
$X^1$ of said antagonist is a methionine residue; and
$X^2$ of said antagonist is a valine residue.

24. A method in accordance with claim 22 wherein
$R^1$ of said antagonist is H;
$R^2$ of said antagonist is H;
$X^1$ of said antagonist is a norleucine residue; and
$X^2$ of said antagonist is a valine residue.

25. A pharmaceutical composition comprising a pharmaceutically acceptable excipient and a vasoactive intestinal polypeptide (VIP) antagonist, said antagonist consisting of the following amino acid sequence:

$R^1$—Lys—Pro—Arg—Arg—Pro—Tyr—Thr—Asp—Asn—Tyr—Thr—Arg—Leu—Arg—Lys—Gln—$X^1$—Ala—$X^2$—Lys—Lys—Tyr—Leu—Asn—Ser—Ile—Leu—AsnNH—$R^2$ in which:
$R^1$ and $R^2$ are members independently selected from the group consisting of hydrogen, $C_1$ to $C_{20}$ alkyl and $C_1$ to $C_{20}$ acyl, provided that at least one of $R^1$ or $R^2$ is hydrogen; and
$X^1$ and $X^2$ are members independently selected from the group consisting of naturally occuring amino acids and amino acid mimetics of hydrophobic character;
and conservative modifications thereof, with the proviso that said antagonist is not the following compound:

Lys-Pro-Arg-Arg-Pro-Tyr-Thr-Asp-Asn-Tyr-Thr-Arg-Leu-Arg-Lys-Gln-Met-Ala-Val-Lys-Lys-Tyr-Leu-Asn-Ser-Ile-Leu-Asn.

26. A method of inhibiting the growth of VIP receptor containing tumor cells selected from the group consisting of lung tumor cells and breast tumor cells, said method comprising administering to said mammal a vasoactive intestinal polypeptide (VIP) antagonist in an amount sufficient to effect said inhibition, said antagonist consisting of the following amino acid sequence:

$R^1$—Lys—Pro—Arg—Arg—Pro—Tyr—Thr—Asp—Asn—Tyr—Thr—Arg—Leu—Arg—Lys—Gln—$X^1$—Ala—$X^2$—Lys—Lys—Tyr—Leu—Asn—Ser—Ile—Leu—AsnNH—$R^2$ in which:
$R^1$ and $R^2$ are members independently selected from the group consisting of hydrogen, $C_1$ to $C_{20}$ alkyl and $C_1$ to $C_{20}$ acyl, provided that at least one of $R^1$ or $R^2$ is hydrogen; and
$X^1$ and $X^2$ are members independently selected from the group consisting of naturally occurring amino acids and amino acid mimetics of hydrophobic character;
and conservative modifications thereof, with the proviso that said antagonist is not the following compound:

Lys-Pro-Arg-Arg-Pro-Tyr-Thr-Asp-Asn-Tyr-Thr-Arg-Leu-Arg-Lys-Gln-Met-Ala-Val-Lys-Lys-Tyr-Leu-Asn-Ser-Ile-Leu-Asn.

* * * * *